(12) United States Patent
Garcia Sanz et al.

(10) Patent No.: US 8,946,166 B2
(45) Date of Patent: Feb. 3, 2015

(54) PEPTIDE-BASED COMPOUNDS AND COMPOSITIONS WHICH INHIBIT MUSCLE CONTRACTION

(75) Inventors: Nuria Garcia Sanz, Alicante (ES); Wim Van Den Nest, Barcelona (ES); Cristina Carreno Serraima, Barcelona (ES); Antonio Ferrer Montiel, Alicante (ES); Juan Cebrian Puche, Becelona (ES); Nuria Alminana Domenech, Barcelona (ES); Gregorio Fernandez Ballester, Murcia (ES)

(73) Assignee: Lipotec, S.A., Gava-Barcelona (ES)

( * ) Notice: Subject to any disclaimer, the term of this patent is extended or adjusted under 35 U.S.C. 154(b) by 396 days.

(21) Appl. No.: 13/384,557

(22) PCT Filed: Jul. 23, 2010

(86) PCT No.: PCT/EP2010/004530
§ 371 (c)(1),
(2), (4) Date: Jan. 17, 2012

(87) PCT Pub. No.: WO2011/009626
PCT Pub. Date: Jan. 27, 2011

(65) Prior Publication Data
US 2012/0121675 A1 May 17, 2012

Related U.S. Application Data

(60) Provisional application No. 61/228,767, filed on Jul. 27, 2009.

(30) Foreign Application Priority Data

Jul. 24, 2009 (ES) .................................. 200930501

(51) Int. Cl.
| | |
|---|---|
| A61K 38/08 | (2006.01) |
| A61K 38/03 | (2006.01) |
| A61K 8/64 | (2006.01) |
| A61Q 19/00 | (2006.01) |
| C07K 7/06 | (2006.01) |
| C07K 14/47 | (2006.01) |
| A61K 38/00 | (2006.01) |

(52) U.S. Cl.
CPC . *A61K 38/08* (2013.01); *C07K 7/06* (2013.01); *A61K 8/64* (2013.01); *A61Q 19/00* (2013.01); *C07K 14/4703* (2013.01); *A61K 38/00* (2013.01)
USPC ....... 514/18.8; 514/21.6; 514/21.7; 514/21.8; 424/401; 424/78.02; 424/70.14

(58) Field of Classification Search
None
See application file for complete search history.

(56) References Cited

U.S. PATENT DOCUMENTS

| | | |
|---|---|---|
| 6,169,074 B1 | 1/2001 | Montal et al. |
| 6,780,413 B2 | 8/2004 | Hott et al. |
| 7,473,679 B2 | 1/2009 | Blanes Mira et al. |
| 7,964,630 B2 | 6/2011 | Imfeld et al. |

FOREIGN PATENT DOCUMENTS

| | | |
|---|---|---|
| EP | 1180524 | 8/2006 |
| WO | 9734620 | 9/1997 |
| WO | 2006047900 | 5/2006 |

OTHER PUBLICATIONS

International Search Report for PCT/EP2010/004530, Completed by the European Patent Office on Dec. 6, 2010, 3 Pages.
Smith et al. 1999, 5th edition, 111 Pages, "March's Advanced Organic Chemistry Reactions, Mechanisms, and Structure."
Kullmann. The Journal of Biological Chemistry Issue of Sep. 10, 1980, vol. 255, No. 17, p. 8234-8238, "Proteases as Catalysts for Enzymic Syntheses of Opioid Peptides."
Lloyd-Williams et al. Tetragedron 1993, vol. 49, No. 48, p. 11065-11133, "Tetrahedron Report No. 347, Convergent Solid-Phase Peptide Synthesis."
Barlos et al. Tetrahedron Letters 1989, vol. 30, No. 30, p. 3943-3946, "Darstellung Geschutzter Peptid-Fragmente Unter Einsatz Substituierter Triphenylmethyl-Harze."
Barlos et al. Tetrahedron Letters 1989, vol. 30, No. 30, p. 3947-3950, "Veresterung Von Partiell Geschutzten Peptid-Fragmenten Mit Harzen. Einsatz Von 2-Chlortritylchlorid Zur Synthese Von Leu 15—Gastrin I."
Schabb. Happi, May 1986, p. 84-86, "Impregnating Fabrics With Microcapsules."
Nelson. International Journal of Pharmaceutics 2002, vol. 242, p. 55-62, "Application of microencapsulation in textiles."
Albericio et al. J. Org. Chem. 1990, vol. 55, p. 3730-3743, "Preparation and Application of the 5-(4-(9-Fluorenylmethyloxycarbonyl)aminomethyl-3,5-dimethoxyphenoxy)-valeric Acid (PAL) Handle for the Solid-Phase Synthesis of C-Terminal Peptide Amides under Mild Conditions 1-3."
Matsueda et al. Peptides 1981, vol. 2, p. 45-50, "A p-Methylbenzhydrylamine Resin for Improved Solid-Phase Syntheis of Peptide Amides."
Berge et al. Journal of Pharmaceutical Sciences Jan. 1977, vol. 66, No. 1, p. 1-19, "Review Article, Pharmaceutical Salts."

(Continued)

*Primary Examiner* — Kevin S Orwig
(74) *Attorney, Agent, or Firm* — Fay Sharpe LLP

(57) ABSTRACT

Peptides of general formula (I): $R_1-W_n-X_m-AA_1-AA_2-AA_3-AA_4-AA_5-AA_6-Y_p-Z_s-R_2$ their stereoisomers, mixtures thereof and/or their cosmetically or pharmaceutically acceptable salts, their preparation process, cosmetic or pharmaceutical compositions which contain them and their use in the treatment and/or care of conditions, disorders and/or diseases that are a consequence of muscle contraction.

22 Claims, No Drawings

(56) References Cited

OTHER PUBLICATIONS

Lloyd-Williams et al. Chemical Approaches to the Synthesis of Peptides and Proteins 1997, 78 Pages, "Solid-Phase Peptide Synthesis."
Kaiser et al. Anal. Biochem. 1970, vol. 34, p. 595-598, "Color Test for Detection of Freee Terminal Amino Groups in the Solid-Phase Synthesis of Peptides."
Stewart et al. Solid Phase Peptide Synthesis 1984 second edition 1984, "The Chemistry of Solid Phase Peptide Synthesis.", All together 20 Pages.
Bodanszky et al. The Practice of Peptide Synthesis second edition 1984, "Activation and Coupling", All together 54 Pages.
Greene et al. Protective Groups in Organic Synthesis third edition, 1999, "The Role of Protective Groups in Organic Synthesis.", All together 20 Pages.
Atherton et al. The Practical Approach Series 1989, All together 17 Pages, "Solid Phase peptide synthesis, a practical approach."
Wang. Journal of the American Chemical Society Feb. 21, 1973, vol. 95, No. 4, p. 1328-1333 "p-Alkoxybenzyl Alcohol Resin and P-Alkoxybenzyloxycarbonylhydrazide Resin for Solid Phase Synthesis of Protected Peptide Fragments."
Remington, 21st edition, 2005, "The Science and Practice of Pharmacy." 60 Pages.
Fauli. Treated Galenic Pharmacy 1993, "Pharmaceutical Technology", English translation of first paragraph, 8 Pages.
Hipler et al. Biofunctional Textiles and the Skin 2006, vol. 33, 10 Pages, "Current Problems in Dermatology."
Gottschalck et al. International Cosmetic Ingredient Dictionary and Handbook, 12th edition 2008, vol. 3, 14 Pages, "Biological Polymers and their Derivatives (Including salts, excluding gums, hydrophilic colloids and derivatives)."
Dweck. R.G. Harry Cosmeticology 8th edition, 2000, 27 Pages, "Botanicals in Cosmetics & Toiletries."
Joint Commussion on Biochemical Nomenclature Eur. J. Biochem. 1984, vol. 138, p. 9-37, "Nomenclature and Symbolism for Amino Acids and Peptides."
Lindstrom., Molecular Neurobiology 1997, vol. 15, p. 193-222, "Nicotinic Acetylcholine Receptors in Health and Disease."
Hoch., Eur. J. Biochem. 1999, vol. 265, p. 1-10, "Formation of the neuromuscular junction, Agrin and its unusual receptors."
Mittaud et al. Molecular and Cellular Biology Sep. 2004, vol. 24, No. 18, p. 7841-7854, "A Single Pulse Agrin Triggers a Pathway That Acts to Cluster Acetylcholine Receptors."
Apel et al. Neuron Jul. 1995, vol. 15, p. 115-126, "Rapsyn May Function as a Link between the Acetylcholine Receptor and the Agrin-Binding Dystrophin-Associated Glycoprotein Complex."
Valenzuela et al. Neuron Sep. 1995, vol. 15, p. 573-584, "Receptor Tyrosine Kinase Specific for the Skeletal Muscle Lineage: Expression in Embryonic Muscle, at the Neuromuscular Junction, and after Injury."
Zhou et al. The Journal of Cell Biology Sep. 6, 1999, vol. 146, No. 5, p. 1133-1146, "Distinct Domains of MuSK Mediate Its Abilities to Induce and to Associate with Postsynaptic Specializations."
Chevessier et al. Human Molecular Genetics 2004, vol. 13, No. 24, p. 3229-3240, "MUSK, a new target for mutations causing congenital myasthenic syndrome."
Chevessier et al. Human Molecular Geneteics 2008, vol. 17, No. 22, p. 3577-3595, "A mouse model for congenital myasthenic syndrome due to MuSK mutations reveals defects in structure and function of neuromuscular junctions."
Jinnah et al. Neurotherapeutics: The Journal of the American Society for Experimental NeuroTherapeutics Apr. 2008, vol. 5, p. 198-209, "Experimental Therapeutics for Dystonia."
Christensen., Acta Chemica Scandinavica B 1979, vol. 33, p. 763-766, "A Qualitative Test for Monitoring Coupling Completeness in Solid Phase Peptide Synthesis Using Chloranil."
Samson et al. Biochemistry 2008, vol. 47, p. 4065-4070, "Inhibition Mechanism of the Acetylcholine Receptor by a-Neurotoxins as Revealed by Normal-Mode Dynamics."
Rink, Tetrahedron Letters 1987, vol. 28, No. 33, p. 3787-3790, "Solid-Phase Synthesis of Protected Peptide Fragements Using a Trialkoxy-Diphenyl-Methylester Resin."
Roberts et al. The peptides 1983, vol. 5, Chapter 6, 55 Pages, "Unusual Amino Acids in Peptide Synthesis."
Malcolm et al. "Controlled Release of Model Antibacterial Drug From a Novel Self-Lubricating Silicone Biomaterial", Journal of Controlled Release 2004, vol. 97, p. 313-320.
Gally et al. Nature Sep. 30, 2004, vol. 431, p. 578-582, "A transmembrane protein required for acetylcholine receptor clustering in Caenorhabditis elegans."
Brooke et al. Journal of Neurology, Neurosurgery and Psychiatry 1978, vol. 41, p. 861-864, "A Clinican's View of Neuromuscular Diseases."
Fahn. Advances in Neurology 1988, vol. 50, 8 Pages, "Concept and Classification of Dystonia."
Hopf et al. European Journal of Neuroscience 1997, vol. 9, p. 1170-1177, "Heparin Inhibits Acetylcholine Receptor Aggregation at Two Distinct Steps in the Agrin-induced Pathway."
Klein et al. Neuroscience 2004, vol. 127, p. 563-567, "Inhibition of Nicotinic Acetylcholine Receptors by Apolipoprotein E-Derived Peptides in Rat Hippocampal Slices."
Yumoto et al. Biochemical and Biophysical Research Communications 2005, vol. 331, p. 1522-1527, "The Acetylcholine receptor y-to-e switch occurs in individual endplates."
Layzer. Muscle Pain, Cramps and Fatigue 1986, Chapter 67, p. 1754-1768, "Muscle Pain".

```
SEQUENCE LISTING

<160> NUMBER OF SEQ ID NOS: 28

<210> SEQ ID NO 1
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 1

Asp Asp Tyr Phe Arg Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 2

Asp Asp Tyr Tyr Arg Met
1               5

<210> SEQ ID NO 3
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 3

Asp Asp Tyr Tyr Lys Leu
1               5
```

```
<210> SEQ ID NO 4
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 4

Asp Asp Tyr Tyr Lys Met
1               5

<210> SEQ ID NO 5
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 5

Glu Asp Arg Phe Arg Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 6

Glu Asp Arg Phe Arg Met
1               5

<210> SEQ ID NO 7
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 7

Glu Asp Arg Phe Lys Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 8

Glu Asp Arg Tyr Arg Leu
1               5

<210> SEQ ID NO 9
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 9

Glu Asp Tyr Phe Arg Leu
1               5

<210> SEQ ID NO 10
```

```
<211> LENGTH: 8
<212> TYPE: PRT
<213> ORGANISM: Artificial Sequence
<220> FEATURE:
<223> OTHER INFORMATION: Peptide inhibitor of AChR clustering

<400> SEQUENCE: 10

Glu Asp Tyr Tyr Arg Leu Gly Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Peptide inhibitor of AChR clustering

<400> SEQUENCE: 11

Glu Asp Tyr Tyr Arg Leu Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 12

Glu Asp Tyr Tyr Arg Leu
1               5

<210> SEQ ID NO 13
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 13

Glu Asp Tyr Tyr Arg Met
1               5

<210> SEQ ID NO 14
<211> LENGTH: 8
<212> TYPE: PRT
<213> ORGANISM: Artificial Sequence
<220> FEATURE:
<223> OTHER INFORMATION: Peptide inhibitor of AChR clustering

<400> SEQUENCE: 14

Gly Glu Asp Tyr Tyr Arg Leu Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Peptide inhibitor of AChR clustering

<400> SEQUENCE: 15

Gly Glu Asp Tyr Tyr Arg Leu
1               5

<210> SEQ ID NO 16
<211> LENGTH: 8
```

```
<212> TYPE: PRT
<213> ORGANISM: Artificial Sequence
<220> FEATURE:
<223> OTHER INFORMATION: Peptide inhibitor of AChR clustering

<400> SEQUENCE: 16

Gly Gly Glu Asp Tyr Tyr Arg Leu
1               5

<210> SEQ ID NO 17
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 17

Pro Asp Arg Phe Lys Leu
1               5

<210> SEQ ID NO 18
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 18

Pro Asp Arg Tyr Arg Leu
1               5

<210> SEQ ID NO 19
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 19

Pro Asp Arg Tyr Lys Leu
1               5

<210> SEQ ID NO 20
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 20

Pro Asp Tyr Phe Arg Leu
1               5

<210> SEQ ID NO 21
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 21

Pro Asp Tyr Phe Lys Leu
1               5

<210> SEQ ID NO 22
<211> LENGTH: 6
<212> TYPE: PRT
```

```
<213> ORGANISM: Artificial Sequence
<220> FEATURE:
<223> OTHER INFORMATION: Peptide inhibitor of AChR clustering

<400> SEQUENCE: 22

Pro Asp Tyr Tyr Arg Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 23

Pro Asp Tyr Tyr Arg Met
1               5

<210> SEQ ID NO 24
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 24

Pro Asp Tyr Tyr Lys Leu
1               5

<210> SEQ ID NO 25
<211> LENGTH: 6
<212> TYPE: PRT
<213> ORGANISM: Artificial Sequence
<220> FEATURE:
<223> OTHER INFORMATION: Peptide inhibitor of AChR clustering

<400> SEQUENCE: 25

Pro Asp Tyr Tyr Lys Met
1               5

<210> SEQ ID NO 26
<211> LENGTH: 8
<212> TYPE: PRT
<213> ORGANISM: Artificial Sequence
<220> FEATURE:
<223> OTHER INFORMATION: Peptide inhibitor of AChR clustering

<400> SEQUENCE: 26

Ala Glu Asp Arg Phe Arg Met Gly
1               5

<210> SEQ ID NO 27
<211> LENGTH: 7
<212> TYPE: PRT
<213> ORGANISM: Artificial Sequence
<220> FEATURE:
<223> OTHER INFORMATION: Peptide inhibitor of AChR clustering

<400> SEQUENCE: 27

Glu Asp Tyr Tyr Arg Met Gly
1               5

<210> SEQ ID NO 28
<211> LENGTH: 8
<212> TYPE: PRT
<213> ORGANISM: Artificial Sequence
```

```
<220> FEATURE:
<223> OTHER INFORMATION: Peptide inhibitor of AChR clustering

<400> SEQUENCE: 28

Gly Gly Pro Asp Tyr Tyr Lys Leu
1               5
```

PEPTIDE-BASED COMPOUNDS AND COMPOSITIONS WHICH INHIBIT MUSCLE CONTRACTION

CROSS-REFERENCE TO RELATED APPLICATION

This application is the U.S. national phase of PCT Appln. No. PCT/EP2010/004530 filed Jul. 23, 2010 which claims priority to Spanish application 200930501 filed Jul. 24, 2009, and claims the benefit of U.S. provisional application 61/228, 767 filed on Jul. 27, 2009, the disclosures of which are incorporated in their entirety by reference herein.

SEQUENCE LISTING

The text file is Sequence_Listings.text, created Jan. 4, 2012, and of size 6 KB, filed herewith, is hereby incorporated by reference.

FIELD OF THE INVENTION

This invention relates to peptides capable of inhibiting muscle contraction and to cosmetic or pharmaceutical compositions which contain these peptides useful in the treatment and/or care of the skin, preferably for the treatment and/or care of conditions, disorders and/or diseases which are a consequence of muscle contraction, particularly of acetylcholine receptor clustering.

BACKGROUND OF THE INVENTION

Muscle contraction is the physiological process in which muscles develop tension and are shortened or lengthened (or can also remain the same length) due to a prior excitation stimulus. These contractions produce the motive force of almost all superior animals to, for example, displace the contents of the cavity that they cover (smooth muscles) or move the organism through its environment or to move other objects (striated muscle).

Muscles are formed by contractile multinucleated muscle fibers (syncytes which result from the fusion of several myocytes), arranged forming portions which are innervated by the synaptic buttons in neuronal axons. The junction between neuron and muscle fiber is called a neuromuscular junction or NMJ. Neurons transmit stimuli in the form of action potentials and this causes the release of the neurotransmitter acetylcholine (ACh) to the synaptic cleft. In the postsynaptic part of NMJ there is an accumulation of acetylcholine receptors (AChRs) responsible for receiving the signal and causing the muscle to contract.

AChRs are classified into two large groups according to their binding with specific agonists: nicotinic acetylcholine receptors (nAChRs) and muscarinic acetylcholine receptors (mAChRs). Nicotinic acetylcholine receptors are given this name due to the high affinity with which they bind to the alkaloid nicotine; the muscarinic acetylcholine receptors, however, bind with a high affinity to the alkaloid muscarine. The nicotinic acetylcholine receptors, in turn, can be classified according to their capacity or incapacity to bind α-bungarotoxin. nAChRs are ionotropic receptors, i.e., they are coupled to ionic channels whose pathway is opened by the ligand binding. mAChRs are metabotropic type receptors or receptors which are coupled to G proteins: in their case the circulation of ions depends on one or various metabolic pathways triggered by the ligand binding.

The neuromuscular junction has classically been used as a general neurotransmission model and therefore its functioning is described in detail. An action potential arrives at the terminal part of the motor neuron and causes the voltage-dependent calcium channels to open in the presynaptic membrane, with a resulting local intracellular increase in calcium. The $Ca^{2+}$ ions bind to proteins which link the synaptic vesicles, full of neurotransmitter ACh, to the plasma membrane. In this case, the synaptobrevin protein binds strongly to syntaxin and SNAP-25, forming the SNARE complex (SyN-aptosomal-Associated Protein Receptor), which enables the fusion between vesicular and plasma membranes and causes exocytosis of ACh to the synaptic cleft. This neurotransmitter spreads through the synaptic space and binds to the AChRs in the postsynaptic membrane. The binding of ACh (or another agonist) causes the channel to open and this enables the circulation of sodium ions towards to inside of the cell and the potassium to leave. The entrance of sodium causes a depolarization which is transmitted through the cell membrane until it arrives at the specialized areas that trigger the release of calcium from endoplasmic reticulum towards the cytosol which induces the contraction of the muscle.

At a molecular level, the nAChRs are pentameric proteins formed by 5 monomers arranged in radial symmetry and forming a pore 2.5 nm in diameter. These sub-units are generally found in a stoichiometry $(\alpha)_2$-β-γ-δ, and 17 types of subunits have been described: 10 types of α-called α1 to α10-, 4 types of subunit β-called β1 to β4-, γ, δ, and ε [Lindstrom J. (1997) "*Nicotinic acetylcholine receptors in health and disease*" *Mol. Neurobiol.* 15:193-222]. The molecular composition at a sub-unit level finely determines the functionality of the receptor: in the neuromuscular junction, for example, the nAChRs are heteropentameric $(\alpha 1)_2$-β1-γ-δ in the embryonic phase, whilst in the adult phase they are heteropentameric $(\alpha 1)_2$-β1-δ-ε. The change of sub-unit γ to ε has been related to the maturation of the neuromuscular junction, and with the maintenance of the structure in adult muscle [Yumoto N., Wakatsuki S. and Sehara-Fujisawa A. (2005) "*The acetylcholine receptor gamma-to-epsilon switch occurs in individual endplates*" *Biochem. Biophys. Res. Commun.* 331:1522-1527].

The neuromuscular junction is a specialized structure whose function is to ensure an efficient and rapid transmission of an action potential in order to cause depolarization in the postsynaptic muscle, which is the signal required for this to contract itself. To achieve a rapid transfer of information between neuron and muscle fiber a correct spatial disposition of the presynaptic zone with the postsynaptic membrane is required. The presynaptic part is characterized by the presence of ACh vesicles, whilst almost all the muscle fiber AChRs are concentrated and are densely packed in the postsynaptic part. The AChRs cluster in a complex process which is key in the formation of the NMJ and its maintenance [Hoch W. (1999) "*Formation of the neuromuscular junction. Agrin and its unusual receptors*" *Eur. J. Biochem.* 265:1-10].

AChR clustering requires the interaction of various proteins, of which three should be highlighted: agrin, MuSK (muscle-specific kinase) and rapsyn. The protein agrin is believed to be responsible for triggering the pathway which leads to the clustering of receptors [Mittaud P., Camilleri A. A., Willmann R., Erb-Vögtli S., Burden S. J. and Fuhrer C. (2004) "*A single pulse of agrin triggers a pathway that acts to cluster acetylcholine receptors*" *Mol. Cell Biol.* 18:7841-7854], and which results in phosphorylation, clustering and stabilization of AChRs. The protein rapsyn is capable of inducing AChR clustering in culture and it has been demonstrated that in mutants deficient for rapsyn the formation of AChR clusters is inhibited [Apel E. D., Roberds S. L., Campbell K. P. and Merlie J. P. (1995) "*Rapsyn may function as a link between the acetylcholine receptor and the agrin-binding dystrophin-associated glycoprotein complex*" Neuron 1:115-126]. The factor that links agrin and rapsyn is MuSK [Valenzuela D. M., Stitt T. N., DiStefano P. S., Rojas E., Mattsson K., Compton D. L., Nuñez L., Park J. S., Stark J. L., Gies D. R., Thomas S., Le Beau M. M., Fernald A. A., Copeland N. G., Jenkins N. A., Burden S. J., Glass D. J. and Yancopoulos G. D. (1995) "*Receptor tyrosine kinase specific for the skeletal muscle lineage: Expression in embryonic muscle, at the neuromuscular junction, and after injury*" Neuron 3:573-584]. MuSK is a receptor with kinase activity which phosphorylates the protein agrin in an interaction which requires an additional component called MASC (muscle associated specificity component). The activation of MuSK through the binding of this ligand is not sufficient on its own to cause AChR clustering, and an interaction between MuSK and rapsyn has been proposed which would be mediated by a factor called RATL (rapsyn associated transmembrane linking molecule), through which the AChR-rapsyn complex could interact with the agrin-MASC-MuSK complex and form the postsynaptic apparatus of mature NMJs [Zhou H., Glass D. J., Yancopoulos G. D. and Sanes J. R. (1999) "*Distinct domains of MuSK mediate its abilities to induce and to associate with postsynaptic specializations*" J. Cell Biol. 146:1133-1146]. It has been found that the gene which codifies MuSK is disturbed in severe muscular diseases such as congenital myasthenic syndrome, a disease caused by a decrease in neurotransmission in which patients suffer from muscle weakness [Chevessier F., Faraut B., Ravel-Chapuis A., Richard P., Gaudon K., Bauché S., Prioleau C., Herbst R., Goillot E., Ioos C., Azulay J. P., Attarian S., Leroy J. P., Fournier E., Legay C., Schaeffer L., Koenig J., Fardeau M., Eymard B., Pouget J. and Hantaî D. (2004) "*MUSK, a new target for mutations causing congenital myasthenic syndrome*" Hum. Mol. Genet. 13:3229-3240], and the relevant role of MuSK in this disease has been confirmed through the establishment of a mouse model in which the MuSK gene lacked its kinase domain and that also shows a phenotype with muscle weakness [Chevessier F., Girard E., Molgó J., Bartling S., Koenig J., Hantaî D. and Witzemann V. (2008) "*A mouse model for congenital myasthenic syndrome due to MuSK mutations reveals defects in structure and function of neuromuscular junctions*" Hum. Mol. Genet. 17:3577-3595].

Muscle contractions are controlled by the central nervous system; the brain controls voluntary contractions, whilst the spinal cord controls involuntary reflexes. Both processes are mediated by the regulated release of the neurotransmitter acetylcholine. However, different disorders or neurological diseases are characterized by involuntary muscle spasms or dystonia, in which the muscles excessively contract in a sustained way [Fahn S. (1988) "*Concept and classification of dystonia*" Adv. Neurol. 50:1-8]. The appearance of the movements depends on the muscles involved and strength of the contraction. In its weakest form, dystonia can appear to be a simple exaggeration of a movement which would be considered normal, whilst in its most severe form dystonia can even cause abnormal postures of the limbs which are disabling. Depending on the parts of the body which are affected, dystonia is classified as (1) focal dystonia, localized in a specific part of the body, comprising, among others, dystonia of the periocular muscle or blepharospasm, cervical dystonia or spasmodic torticollis, laryngeal dystonia or spasmodic dysphonia, oromandibular dystonia, focal hand dystonia such as writer's or musician's cramp or dystonia of the feet, bruxism, hemifacial spasm, tics and strabismus; (2) generalized dystonia, which affects the greater part or the whole body; (3) multifocal dystonia, which involves two or more unrelated parts of the body; (4) segmental dystonia, which affects two or more adjacent parts of the body, comprising Meige's Syndrome, and (5) hemidystonia, which involves the arm and leg of the same side, comprising dystonia resulting from a stroke [Jinnah H. A. and Hess E. J. (2008) "*Experimental therapeutics for dystonia*" Neurotherapeutics 5:198-209; Brooke M. H. (1986) "*A clinician's view of neuromuscular diseases*" Baltimore, Williams & Wilkins; Layzer R. B. (1986) "*Muscle pain, cramps and fatigue*" in Myology, A G, Engel, B Q Banker, eds, New York, McGraw-Hill].

On the other hand, the repeated contraction of the facial muscles, which are those that transmit expression onto the face, lead to creases in specific areas. With age, from approximately thirty years of age, the appearance of wrinkles or expression lines start to become visible in these areas: furrows, more or less linear, arranged perpendicularly to the direction of the muscle fibers, caused by the disappearance of cells in the skin's dermal layer in these areas. Their depth depends on the individual's age, and the frequency and strength of the muscle contractions which cause the crease. The principle muscles involved in the appearance of expression lines are those surrounding the eyes and eyelashes, those on the forehead, the lip, mouth, cheek and neck muscles. These muscles are found in the subcutaneous connective frontal part of the face, from where they rise towards the skin and insert themselves in the deepest part of the dermal stratum. Their contraction can lead to raising, depressing, constricting or dilatory movements of the skin. The early appearance of wrinkles is the most characteristic sign of age and aging of the skin. Aging of the skin is a process which has two principal components: the chronological component, which is due to the passing of time, and the photo-induced or photoaging component, which is due to the level of exposure to ultraviolet radiation (UV). The sum of several environmental factors such as exposure to tobacco smoke, exposure to pollution, and climate conditions such as cold and/or wind also contributes to the skin's aging. The terms "aging" and "photoaging" of the skin refer to the visible changes in the appearance of the skin such as wrinkles, fine lines, roughness, expression lines, stretch marks, discontinuities, furrows, flaccidity, sagging of the skin such as sagging cheeks, loss of resilience, loss of firmness, elastosis, keratosis, and loss of smoothness.

Since the 1990s, the use of the toxins *Clostridium botulinum* (marketed as Botox® by Allergan) injected into the muscle to reduce muscle contraction and to treat associated diseases such as dystonia and/or pain. Neurotoxin injections have also been used to treat and/or care for the skin with the aim of reducing, delaying or preventing the signs of aging and/or photoaging and in particular to relax the facial expression and reduce the formation of wrinkles or minimize their appearance. Its action mechanism is based on blocking ACh release in the presynaptic terminal of the axon in the neuromuscular junction, thus avoiding nerve transmission and muscle contraction. The toxin binds to receptors in the presynaptic membrane, is internalized and becomes cytoplasm. Its activity is responsible for breaking the trimolecular synaptobrevin SNARE complex, SNAP-25 and syntaxin, which avoids the binding of synaptic vesicles to plasmalemma and releasing ACh to the synaptic cleft.

Although it has been demonstrated that the effects of the botulinum neurotoxin are very lasting, since they take several weeks to reestablish a completely functional innervation of the muscle after the irreversible destruction of the SNARE complex, its administration is not risk free. The main risk is that of its toxicity: even doses lower than 50 μg are lethal for an adult human being. The botulinum neurotoxin causes muscle paralysis, and can even cause death due to cardiac arrest. Administration of the botulinum toxin should, therefore, be carried out by a specialist due to the intrinsic danger of the substance as well as the administration method: direct injection into the muscle. The blocking of the nerve transmission at AChR level through botulinum toxin is not specific enough to just inhibit muscle contraction, but it has other activities which may be undesired by the patient and can cause secondary effects such as nausea, pain or erythema.

The pharmaceutical field has also used other compounds for the inhibition of muscle contraction, including modulators of the gamma-aminobutyric receptor (GABA) such as baclofen or benzodiazepines, agonists of the $\alpha_2$-adrenergic receptors such as tizanidine or clonidine, modulators of AChRs such as the alkaloids derived from curare, specific antibodies against AChRs such as those described in U.S. Pat. No. 6,780,413 B2 or agonists of the ryanodine receptor such as dantrolene. None of these treatments is free from secondary effects, since many of them act at a central nervous system level and may cause dizzy spells, sedation and even addiction in continued treatments.

The cosmetic industry has also carried out different efforts to develop new compounds for the treatment of expression lines and, therefore, to treat and/or care for the skin with the aim of reducing, delaying or preventing the signs of aging and/or photoaging through topical application which avoids the potential secondary effects which occur after injecting botulinum toxin and are, therefore, safer. Different products aimed at the inhibition of the neuromuscular junction at a synaptic level to avoid the appearance or to soften expression lines are described in the prior art. The patents EP 1180524 B1 and WO9734620 describe the use of peptides derived from the protein SNAP-25 which act pre-synaptically competing with SNAP-25 in the formation of the SNARE complex, causing a reduction in the release of ACh and inhibiting the neuronal transmission in the NMJ. Patent EP 1809652 A2 describes antagonist peptides of AChRs which act post-synaptically with a mechanism of action similar to waglerin-1 to block the nerve transmission and prevent the appearance of wrinkles. The active cosmetic pentapeptide-3 also acts post-synaptically by inhibiting AChRs, with a mechanism of action similar to tubocurarine to block the nerve transmission and prevent the appearance of wrinkles.

However, none of the compounds developed by the cosmetic or pharmaceutical field is capable of inhibiting muscle contraction with effectiveness similar to that of botulinum toxin, but in a way that is risk free. Thus there is still a need to identify new agents capable of inhibiting muscle contraction for their co-administration with existing agents in order to achieve better results in the treatment of dystonias as well as in the reduction and/or softening of wrinkles, and in particular, expression lines and, therefore, treat and care for the skin with the aim of reducing, delaying or preventing the signs of aging and/or photoaging.

DETAILED DESCRIPTION OF THE INVENTION

This invention provides a solution to the above-mentioned problem. Surprisingly the applicant of this invention has found that certain synthetic peptides present an important effectiveness in the inhibition of AChR clustering and therefore are useful for the treatment and/or care of those conditions, disorders and/or diseases which are a consequence of muscle contraction, particularly of acetylcholine receptor clustering, as well as the treatment and/or care of the skin.

DEFINITIONS

In order to facilitate the comprehension of this invention, the meanings of some terms and expressions as they are used in the context of the invention are included.

Within the context of this invention "skin" is understood to be the layers which comprise it from the outermost layer or stratum corneum to the lowermost layer or hypodermis, both inclusive. These layers are comprised by different types of cells such as keratinocytes, fibroblasts, melanocytes and/or adipocytes among others.

Within the context of this invention the "care of the skin" comprises the prevention of the signs of aging and/photoaging.

Within this description the abbreviations used for amino acids follow the IUPAC-IUB Joint Commission on Biochemical Nomenclature rules outlined in *Eur. J. Biochem.* (1984) 138:9-37 and in *J. Biol. Chem.* (1989) 264:633-673.

Thus, for example, Asp represents $NH_2$—CH($CH_2COOH$)—COOH, Asp-represents $NH_2$—CH($CH_2COOH$)—CO—, -Asp represents —NH—CH($CH_2COOH$)—COOH and -Asp-represents —NH—CH($CH_2COOH$)—CO—. Therefore, the dash, which represents the peptide bond, eliminates the OH of the 1-carboxyl group of the amino acid (represented here in the non-ionized conventional form) when located at the right of the symbol, and eliminates the H of the 2-amino group of the amino acid when located at the left of the symbol; both modifications can be applied to the same symbol (see Table 1).

TABLE 1

Amino acid structures and their three letter nomenclature code.

| Symbol | Remainder |
|--------|-----------|
| -Arg-  | [structure] |
| -Leu-  | [structure] |
| -Phe-  | [structure] |

TABLE 1-continued

Amino acid structures and their three letter nomenclature code.

| Symbol | Remainder |
|---|---|
| -Lys- | (structure: amino acid backbone with side chain –CH₂CH₂CH₂CH₂–NH₂) |
| -Asp- | (structure: amino acid backbone with side chain –CH₂–COOH) |
| -Pro- | (structure: proline ring) |
| -Met- | (structure: amino acid backbone with side chain –CH₂CH₂–S–CH₃) |
| -Glu- | (structure: amino acid backbone with side chain –CH₂CH₂–COOH) |
| -Tyr- | (structure: amino acid backbone with side chain –CH₂–C₆H₄–OH) |

The abbreviation "Ac-" is used in this description to name the acetyl group ($CH_3$—CO—) and the abbreviation "Palm-" is used to name the palmitoyl group ($CH_3$—$(CH_2)_{14}$—CO—)

The term "non-cyclic aliphatic group" is used in this invention to cover, for example, and not restricted to, linear or branched alkyl, alkenyl and alkynyl groups.

The term "alkyl group" relates to a saturated, linear or branched group, which has between 1 and 24, preferably between 1 and 16, more preferably between 1 and 14, even more preferably between 1 and 12, and even more preferably still 1, 2, 3, 4, 5 or 6 carbon atoms and which is bound to the rest of the molecule by a single bond, including, for example, and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" relates to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon double bonds, preferably with 1, 2 or 3 conjugated or unconjugated carbon-carbon double bonds, which is bound to the rest of the molecule through a single bond, including, for example, and not restricted to, the vinyl, oleyl, linoleyl and similar groups.

The term "alkynyl group" relates to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon triple bonds, preferably with 1, 2 or 3 conjugated or unconjugated carbon-carbon triple bonds, which is bound to the rest of the molecule through a single bond, including, for example, and not restricted to, the ethinyl group, 1-propinyl, 2-propinyl, 1-butinyl, 2-butinyl, 3-butinyl, pentinyl, such as 1-pentinyl and similar groups.

The term "alicyclic group" is used in this invention to cover, for example, and not restricted to, cycloalkyl or cycloalkenyl or cycloalkynyl groups.

The term "cycloalkyl" relates to a saturated mono- or polycyclic aliphatic group which has between 3 and 24, preferably between 3 and 16, more preferably between 3 and 14, even more preferably between 3 and 12, even more preferably still 3, 4, 5 or 6 carbon atoms and which is bound to the rest of the molecule through a single bond, including, for example, and not limited to, cyclopropyl, cyclobutyl, cyclopentyl, cyclohexyl, cycloheptyl, methyl cyclohexyl, dimethyl cyclohexyl, octahydroindene, decahydronaphthalene, dodecahydro-phenalene and similar.

The term "cycloalkenyl" relates to a non-aromatic mono- or polycyclic aliphatic group which has between 5 and 24, preferably between 5 and 16, more preferably between 5 and 14, even more preferably between 5 and 12, even more preferably still 5 or 6 carbon atoms, with one or more carbon-carbon double bonds, preferably with 1, 2 or 3 conjugated or unconjugated carbon-carbon double bonds, which is bound to the rest of the molecule through a single bond, including, for example, and not restricted to, the cyclopent-1-en-1-yl group and similar groups.

The term "cycloalkynyl" relates to a non-aromatic mono- or polycyclic aliphatic group which has between 8 and 24, preferably between 8 and 16, more preferably between 8 and 14, even more preferably between 8 and 12, even more preferably still 8 or 9 carbon atoms, with one or more triple carbon-carbon bonds, preferably 1, 2 or 3 triple conjugated or unconjugated carbon-carbon bonds, which is bound to the rest of the molecule by a simple bond, including, for example, and not restricted to, the cyclooct-2-yn-1-yl group and similar groups.

The term "aryl group" relates to an aromatic group which has between 6 and 30, preferably between 6 and 18, more preferably between 6 and 10, even more preferably 6 or 10 carbon atoms, which comprise 1, 2, 3 or 4 aromatic rings, bound by a carbon-carbon bond or fused, including, for example, and not restricted to, phenyl, naphthyl, diphenyl, indenyl, phenanthryl or anthranyl among others; or an aralkyl group.

The term "aralkyl group" relates to an alkyl group substituted with an aromatic group, with between 7 and 24 carbon atoms and including, for example, and not restricted to, —(CH$_2$)$_{1-6}$-phenyl, —(CH$_2$)$_{1-6}$-(1-naphthyl), —(CH$_2$)$_{1-6}$-(2-naphthyl), —(CH$_2$)$_{1-6}$—CH(phenyl)$_2$ and similar.

The term "heterocyclyl group" relates to a heterocycle or 3-10 member hydrocarbon ring, in which one or more of the ring atoms, preferably 1, 2 or 3 of the ring atoms, is a different element to carbon, such as nitrogen, oxygen or sulfur and may be saturated or unsaturated. For the purposes of this invention, the heterocycle can be a cyclic, monocyclic, bicyclic or tricyclic system which may include fused ring systems; and the nitrogen, carbon or sulfur atoms can be optionally oxidized in the heterocyclyl radical; the nitrogen atom can optionally be quaternized; and the heterocyclyl radical may be partially or completely saturated or may be aromatic. With increasing preference, the term heterocyclyl relates to a 5 or 6 member ring.

The term "heteroarylalkyl group" relates to an alkyl group substituted with a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example, and not restricted to, —(CH$_2$)$_{1-6}$-imidazolyl, —(CH$_2$)$_{1-6}$-triazolyl, —(CH$_2$)$_{1-6}$-thienyl, —(CH$_2$)$_{1-6}$-furyl, —(CH$_2$)$_{1-6}$-pyrrolidinyl and similar.

As used in this technical area, there may be a certain degree of substitution on the groups defined above. Therefore, there can be substitution in any of the groups of this invention. The references in this document to groups substituted in the groups of this invention indicate that the radical specified can be substituted in one or more available positions by one or more substituents, preferably in 1, 2 or 3 positions, more preferably in 1 or 2 positions, even more preferably in 1 position. These substituents include, for example, and not restricted to, alkyl C$_1$-C$_4$; hydroxyl; alcoxyl C$_1$-C$_4$; amino; aminoalkyl C$_1$-C$_4$; carbonyloxyl C$_1$-C$_4$; oxycarbonyl C$_1$-C$_4$; halogen such as fluorine, chlorine, bromine and iodine; cyano; nitro; azido; alkylsulfonyl C$_1$-C$_4$; thiol; alkylthio C$_1$-C$_4$, aryloxyl such as phenoxyl; —NR$_b$(C=NR$_b$)NR$_b$R$_c$; wherein R$_b$ and R$_c$ are selected independently from the group consisting of H, alkyl C$_1$-C$_4$, alkenyl C$_2$-C$_4$, alkynyl C$_2$-C$_4$, cycloalkyl C$_3$-C$_{10}$, aryl C$_6$-C$_{18}$, aralkyl C$_7$-C$_{17}$, 3-10-membered-heterocyclyl or protective group of the amino group.

Compounds of the Invention

The compounds of the invention are defined by the general formula (I)

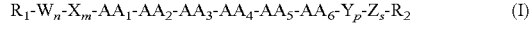

$$R_1\text{-}W_n\text{-}X_m\text{-}AA_1\text{-}AA_2\text{-}AA_3\text{-}AA_4\text{-}AA_5\text{-}AA_6\text{-}Y_p\text{-}Z_s\text{-}R_2 \quad (I)$$

their stereoisomers, mixtures thereof and/or their cosmetically or pharmaceutically acceptable salts, characterized in that:

AA$_1$ is selected from the group consisting of -Asp-, -Glu- and -Pro-;
AA$_2$ is -Asp-;
AA$_3$ is selected from the group consisting of -Tyr- and -Arg-;
AA$_4$ is selected from the group consisting of -Phe- and -Tyr-;
AA$_5$ is selected from the group consisting of -Arg- and -Lys-;
AA$_6$ is selected from the group consisting of -Leu- and -Met-;
W, X, Y and Z are independently selected from amongst themselves from the group consisting of the coded amino acids and non-coded amino acids;
n, m, p and s are independently selected from amongst themselves and have a value of between 0 and 1;

R$_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—; wherein R$_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl; and R$_2$ is selected from the group consisting of —NR$_3$R$_4$, —OR$_3$ and —SR$_3$; wherein R$_3$ and R$_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

The R$_1$ and R$_2$ groups are respectively bound to the amino-terminal (N-terminal) and carboxy-terminal (C-terminal) ends of the peptide sequences According to a preferred embodiment of this invention, R$_1$ is selected from the group consisting of H or R$_5$—CO—, wherein R$_5$ is selected from the group consisting of substituted or unsubstituted alkyl radical C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{24}$, substituted or unsubstituted cycloalkenyl C$_5$-C$_{24}$, substituted or unsubstituted cycloalkynyl C$_8$-C$_{24}$, substituted or unsubstituted aryl C$_6$-C$_{30}$, substituted or unsubstituted aralkyl C$_7$-C$_{24}$, substituted or unsubstituted heterocyclyl with 3-10 ring members, and substituted or unsubstituted heteroarylalkyl of 2 to 24 carbon atoms and 1 to 3 atoms other than carbon and an alkylic chain of 1 to 6 carbon atoms. More preferably, R$_1$ is selected from H, acetyl, tert-butanoyl, hexanoyl, 2-methylhexanoyl, cyclohexancarboxyl, octanoyl, decanoyl, lauroyl, myristoyl, palmitoyl, stearoyl, oleoyl and linoleoyl. Even more preferably, R$_1$ is H, acetyl, lauroyl, myristoyl or palmitoyl. In an even more preferred embodiment, R$_1$ is acetyl or palmitoyl.

According to another preferred embodiment, R$_2$ is —NR$_3$R$_4$, —OR$_3$ or —SR$_3$, wherein R$_3$ and R$_4$ are independently selected from the group consisting of H, substituted or unsubstituted alkyl C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{24}$, substituted or unsubstituted cycloalkenyl C$_5$-C$_{24}$, substituted or unsubstituted cycloalkynyl C$_8$-C$_{24}$, substituted or unsubstituted aryl C$_6$-C$_{30}$, substituted or unsubstituted aralkyl C$_7$-C$_{24}$, substituted or unsubstituted heterocyclyl with 3-10 ring members and substituted or unsubstituted heteroarylalkyl of 2 to 24 carbon atoms and 1 to 3 atoms other than carbon and an alkylic chain of 1 to 6 carbon atoms. Optionally, R$_3$ and R$_4$ can be bound through a saturated or unsaturated carbon-carbon bond, forming a cycle with the nitrogen atom. More preferably R$_2$ is —NR$_3$R$_4$, or —OR$_3$, wherein R$_3$ and R$_4$ are independently selected from the group consisting of H, substituted or unsubstituted alkyl C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{10}$, substituted or unsubstituted aryl C$_6$-C$_{15}$ and substituted or unsubstituted heterocyclyl with 3-10 ring members, substituted or unsubstituted heteroarylalkyl with 3 to 10 ring members and an alkylic chain of 1 to 6 carbon atoms. More preferably R$_3$ and R$_4$ are selected from the group consisting of H, methyl, ethyl, hexyl, dodecyl or hexadecyl. Even more preferably $R_3$ is H and $R_4$ is selected from the group consisting of H, methyl, ethyl, hexyl, dodecyl or hexadecyl. According to an even more preferable embodiment, $R_2$ is selected from —OH and –NH$_2$.

According to another embodiment of this invention $R_1$ is selected from the group consisting of H, acetyl, lauroyl, myristoyl or palmitoyl, $AA_1$ is -L-Glu-, $AA_2$ is -L-Asp-, $AA_3$ is -L-Tyr-, $AA_4$ is -L-Tyr-, $AA_5$ is -L-Arg-, $AA_6$ is -L-Leu-, and $R_2$ is —NR$_3$R$_4$ or —OR$_3$ wherein $R_3$ and $R_4$ are independently selected from H, methyl, ethyl, hexyl, dodecyl and hexadecyl, preferably $R_2$ is —OH or —NH$_2$. More preferably, $R_1$ is acetyl or palmitoyl and $R_2$ is —NH$_2$.

Even more preferably, n, m, p and s are 0.

According to another embodiment of this invention $R_1$ is selected from the group consisting of H, acetyl, lauroyl, myristoyl or palmitoyl, $AA_1$ is -L-Pro-, $AA_2$ is -L-Asp-, $AA_3$ is -L-Tyr-, $AA_4$ is -L-Tyr-, $AA_5$ is -L-Lys-, $AA_6$ is -L-Leu-, and $R_2$ is —NR$_3$R$_4$ or —OR$_3$ wherein $R_3$ and $R_4$ are independently selected from H, methyl, ethyl, hexyl, dodecyl and hexadecyl, preferably $R_2$ is —OH or —NH$_2$. More preferably, $R_1$ is acetyl or palmitoyl and $R_2$ is —NH$_2$.

Even more preferably, n, m, p and s are 0.

According to another embodiment of this invention $R_1$ is selected from the group consisting of H, acetyl, lauroyl, myristoyl or palmitoyl, $AA_1$ is -L-Glu-, $AA_2$ is -L-Asp-, $AA_3$ is -L-Arg-, $AA_4$ is -L-Phe-, $AA_5$ is -L-Arg-, $AA_6$ is -L-Met-, and $R_2$ is —NR$_3$R$_4$ or —OR$_3$ wherein $R_3$ and $R_4$ are independently selected from H, methyl, ethyl, hexyl, dodecyl and hexadecyl, preferably $R_2$ is —OH or —NH$_2$. More preferably, $R_1$ is acetyl or palmitoyl and $R_2$ is —NH$_2$. Even more preferably, n, m, p and s are 0.

According to another embodiment of this invention $R_1$ is selected from the group consisting of H, acetyl, lauroyl, myristoyl or palmitoyl, $AA_1$ is -L-Glu-, $AA_2$ is -L-Asp-, $AA_3$ is -L-Tyr-, $AA_4$ is -L-Tyr-, $AA_5$ is -L-Arg-, $AA_6$ is -L-Met-, and $R_2$ is —NR$_3$R$_4$ or —OR$_3$ wherein $R_3$ and $R_4$ are independently selected from H, methyl, ethyl, hexyl, dodecyl and hexadecyl, preferably $R_2$ is —OH or —NH$_2$. More preferably, R, is acetyl or palmitoyl and $R_2$ is —NH$_2$.

Even more preferably, n, m, p and s are 0.

According to another embodiment of this invention R, is selected from the group consisting of H, acetyl, lauroyl, myristoyl and palmitoyl, $AA_1$ is -L-Pro-, $AA_2$ is -L-Asp-, $AA_3$ is -L-Tyr-, $AA_4$ is -L-Tyr-, $AA_5$ is -L-Arg-, $AA_6$ is -L-Met-, and $R_2$ is —NR$_3$R$_4$ or —OR$_3$ wherein $R_3$ and $R_4$ are independently selected from H, methyl, ethyl, hexyl, dodecyl and hexadecyl, preferably $R_2$ is —OH or —NH$_2$. More preferably, $R_1$ is acetyl or palmitoyl and $R_2$ is —NH$_2$. Even more preferably, n, m, p and s are 0.

According to another embodiment of this invention $R_1$ is selected from the group consisting of H, acetyl, lauroyl, myristoyl and palmitoyl, preferably $R_1$ is selected from the group consisting of H, acetyl and palmitoyl and $R_2$ is selected from the group consisting of —OH and —NH$_2$.

Preferably, the compounds of formula (I) are selected from the group consisting of:
Ac-Asp-Asp-Tyr-Phe-Arg-Leu-NH$_2$,
Ac-Asp-Asp-Tyr-Phe-Arg-Leu-OH,
Ac-Asp-Asp-Tyr-Tyr-Arg-Met-NH$_2$
Ac-Asp-Asp-Tyr-Tyr-Lys-Leu-NH$_2$,
Ac-Asp-Asp-Tyr-Tyr-Lys-Leu-OH,
Ac-Asp-Asp-Tyr-Tyr-Lys-Met-NH$_2$
Ac-Glu-Asp-Arg-Phe-Arg-Leu-NH$_2$
Ac-Glu-Asp-Arg-Phe-Arg-Met-NH—(CH$_2$)$_{15}$—CH$_3$,
Ac-Glu-Asp-Arg-Phe-Arg-Met-NH$_2$,
Ac-Glu-Asp-Arg-Phe-Arg-Met-OH,
Ac-Glu-Asp-Arg-Phe-Lys-Leu-NH$_2$,
Ac-Glu-Asp-Arg-Phe-Lys-Leu-OH,
Ac-Glu-Asp-Arg-Tyr-Arg-Leu-NH$_2$,
Ac-Glu-Asp-Arg-Tyr-Arg-Leu-OH,
Ac-Glu-Asp-Tyr-Phe-Arg-Leu-NH$_2$,
Ac-Glu-Asp-Tyr-Phe-Arg-Leu-OH,
Ac-Glu-Asp-Tyr-Tyr-Arg-Leu-Gly-Gly-NH$_2$,
Ac-Glu-Asp-Tyr-Tyr-Arg-Leu-Gly-NH$_2$,
Ac-Glu-Asp-Tyr-Tyr-Arg-Leu-NH—(CH$_2$)$_{15}$—CH$_3$,
Ac-Glu-Asp-Tyr-Tyr-Arg-Leu-NH$_2$,
Ac-Glu-Asp-Tyr-Tyr-Arg-Leu-OH,
Ac-Glu-Asp-Tyr-Tyr-Arg-Met-NH—(CH$_2$)$_{15}$—CH$_3$,
Ac-Glu-Asp-Tyr-Tyr-Arg-Met-NH$_2$,
Ac-Glu-Asp-Tyr-Tyr-Arg-Met-OH,
Ac-Gly-Glu-Asp-Tyr-Tyr-Arg-Leu-Gly-NH$_2$,
Ac-Gly-Glu-Asp-Tyr-Tyr-Arg-Leu-NH$_2$,
Ac-Gly-Gly-Glu-Asp-Tyr-Tyr-Arg-Leu-NH$_2$,
Ac-Pro-Asp-Arg-Phe-Lys-Leu-NH$_2$,
Ac-Pro-Asp-Arg-Phe-Lys-Leu-OH,
Ac-Pro-Asp-Arg-Tyr-Arg-Leu-NH$_2$,
Ac-Pro-Asp-Arg-Tyr-Arg-Leu-OH,
Ac-Pro-Asp-Arg-Tyr-Lys-Leu-NH$_2$,
Ac-Pro-Asp-Arg-Tyr-Lys-Leu-OH,
Ac-Pro-Asp-Tyr-Phe-Arg-Leu-NH—(CH$_2$)$_{15}$—CH$_3$
Ac-Pro-Asp-Tyr-Phe-Lys-Leu-NH$_2$
Ac-Pro-Asp-Tyr-Tyr-Arg-Leu-NH$_2$,
Ac-Pro-Asp-Tyr-Tyr-Arg-Leu-OH,
Ac-Pro-Asp-Tyr-Tyr-Arg-Met-NH—(CH$_2$)$_{15}$—CH$_3$,
Ac-Pro-Asp-Tyr-Tyr-Arg-Met-NH$_2$,
Ac-Pro-Asp-Tyr-Tyr-Arg-Met-OH,
Ac-Pro-Asp-Tyr-Tyr-Lys-Leu-NH—(CH$_2$)$_{15}$—CH$_3$,
Ac-Pro-Asp-Tyr-Tyr-Lys-Leu-NH$_2$,
Ac-Pro-Asp-Tyr-Tyr-Lys-Leu-OH,
Ac-Pro-Asp-Tyr-Tyr-Lys-Met-NH$_2$
H-Glu-Asp-Arg-Phe-Arg-Met-NH$_2$
Palm-Ala-Glu-Asp-Arg-Phe-Arg-Met-Gly-NH$_2$;
Palm-Asp-Asp-Tyr-Phe-Arg-Leu-NH$_2$,
Palm-Asp-Asp-Tyr-Phe-Arg-Leu-OH,
Palm-Asp-Asp-Tyr-Tyr-Lys-Leu-NH$_2$,
Palm-Asp-Asp-Tyr-Tyr-Lys-Leu-OH,
Palm-Glu-Asp-Arg-Phe-Arg-Met-NH$_2$,
Palm-Glu-Asp-Arg-Phe-Arg-Met-OH,
Palm-Glu-Asp-Arg-Phe-Lys-Leu-NH$_2$,
Palm-Glu-Asp-Arg-Phe-Lys-Leu-OH,
Palm-Glu-Asp-Arg-Tyr-Arg-Leu-NH$_2$,
Palm-Glu-Asp-Arg-Tyr-Arg-Leu-OH,
Palm-Glu-Asp-Tyr-Phe-Arg-Leu-NH$_2$,
Palm-Glu-Asp-Tyr-Phe-Arg-Leu-OH,
Palm-Glu-Asp-Tyr-Tyr-Arg-Leu-Gly-Gly-NH$_2$,
Palm-Glu-Asp-Tyr-Tyr-Arg-Leu-NH$_2$,
Palm-Glu-Asp-Tyr-Tyr-Arg-Leu-OH,
Palm-Glu-Asp-Tyr-Tyr-Arg-Met-Gly-NH$_2$,
Palm-Glu-Asp-Tyr-Tyr-Arg-Met-NH$_2$,
Palm-Glu-Asp-Tyr-Tyr-Arg-Met-OH,
Palm-Gly-Glu-Asp-Tyr-Tyr-Arg-Leu-NH$_2$,
Palm-Gly-Gly-Pro-Asp-Tyr-Tyr-Lys-Leu-NH$_2$,
Palm-Pro-Asp-Arg-Phe-Lys-Leu-NH$_2$,
Palm-Pro-Asp-Arg-Phe-Lys-Leu-OH,
Palm-Pro-Asp-Arg-Tyr-Arg-Leu-NH$_2$,
Palm-Pro-Asp-Arg-Tyr-Arg-Leu-OH,
Palm-Pro-Asp-Arg-Tyr-Lys-Leu-NH$_2$,
Palm-Pro-Asp-Arg-Tyr-Lys-Leu-OH,
Palm-Pro-Asp-Tyr-Tyr-Arg-Leu-NH$_2$,
Palm-Pro-Asp-Tyr-Tyr-Arg-Leu-OH,
Palm-Pro-Asp-Tyr-Tyr-Arg-Met-NH$_2$,
Palm-Pro-Asp-Tyr-Tyr-Arg-Met-OH,
Palm-Pro-Asp-Tyr-Tyr-Lys-Leu-NH$_2$, and
Palm-Pro-Asp-Tyr-Tyr-Lys-Leu-OH,
their stereoisomers, mixtures thereof and/or their cosmetically or pharmaceutically acceptable salts.

The peptides of this invention can exist as stereoisomers or mixtures of stereoisomers; for example, the amino acids which form them can have an L-, D-configuration or be racemic independently of one another. Therefore, it is possible to obtain isomeric mixtures as well as racemic mixtures or diastereomeric mixtures, or pure diastereomers or enantiomers, depending on the number of asymmetric carbons and which isomers or isomeric mixtures are present. The preferred structures of the peptides of the invention are pure isomers, i.e., enantiomers or diastereomers.

For example, when it is stated that $AA_1$ can be -Glu-, it is understood that $AA_1$ is selected from -L-Glu-, -D-Glu- or mixtures of both, racemic or non-racemic. Likewise, when it is said that $AA_2$ can be -Asp-, it is understood that it can be -L-Asp-, -D-Asp- or mixtures of both, racemic or non-racemic. The preparation processes described in this document allow the person skilled in the art to obtain each of the stereoisomers of the peptide of the invention by choosing the amino acid with the appropriate configuration.

In the context of this invention, the term "non-coded amino acids" refers to any amino acids not codified by the genetic code, natural or unnatural, for example, and not restricted to, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statine, β-alanine, norleucine, N-methyl amino acids, β-amino acids or γ-amino acids among others, as well as their derivates. A list of unnatural amino acids can be found in the article "Unusual amino acids in peptide synthesis" by D. C. Roberts and F. Vellaccio, in The Peptides, Vol. 5 (1983), Chapter VI, Gross E. and Meienhofer J., Eds., Academic Press, New York, USA or in the commercial catalogues of the companies specialized in the field, such as PolyPeptide Laboratories, Bachem, Novabiochem, Sigma-Aldrich, Peptides International, Advanced ChemTech, Chem-Impex, Maybridge Chemical, Chirotech Technology, Peninsula Laboratories or RSP Amino Acid Analogues among others.

In the context of this invention when n, m, p and/or s are different to 0 it is clearly understood that the nature of W, X, Y and/or Z does not make the activity of the peptides of this invention difficult, but it contributes to the inhibition of AChR clustering or it has no effect on it.

In the context of this invention there are also cosmetically or pharmaceutically acceptable salts of the peptides provided by this invention. The term "cosmetically or pharmaceutically acceptable salts" means a salt admitted for its use on animals and, more particularly, human beings, and includes the salts used to form base addition salts, whether inorganic, for example, and not restricted to, lithium, sodium, potassium, calcium, magnesium, manganese, copper, zinc or aluminum among others; or organic for example, and not restricted to, ethylamine, diethylamine, ethylenediamine, ethanolamine, diethanolamine, arginine, lysine, histidine or piperazine among others; or acid addition salts, whether organic, for example, and not restricted to, acetate, citrate, lactate, malonate, maleate, tartrate, fumarate, benzoate, aspartate, glutamate, succinate, oleate, trifluoroacetate, oxalate, pamoate or gluconate among others; or inorganic, for example, and not restricted to chloride, sulfate, borate or carbonate among others. The nature of the salt is not critical, provided that it is cosmetically and pharmaceutically acceptable. Cosmetically and pharmaceutically acceptable salts of the peptides of the invention can be obtained by conventional methods, well known in the prior art [Berge S. M., Bighley L. D. and Monkhouse D. C. (1977) "*Pharmaceutical Salts*" *J. Pharm. Sci.* 66:1-19].

Another aspect of this invention relates to a peptide of general formula (I), its stereoisomers, mixtures thereof, and/ or its cosmetically or pharmaceutically acceptable salts, as described in this invention, for the treatment and/or care of those conditions, disorders and/or diseases which are a consequence of muscle contraction, particularly the clustering of acetylcholine receptors.

In another particular aspect, this invention relates to a peptide of general formula (I), its stereoisomers, mixtures thereof, and/or its cosmetically or pharmaceutically acceptable salts, as described in this invention, for the inhibition of muscle contraction, particularly for the inhibition of acetylcholine receptor clustering.

In another particular aspect, among the disorders and/or diseases to be treated which are a consequence of muscle contraction are dystonias, and more particularly focal dystonias for example, and not restricted to blepharospasm, torsion dystonia, cervical dystonia or torticollis, laryngeal dystonia or spasmodic dysphonia, oromandibular dystonia, dystonia of limbs such as writer's or musician's cramp or dystonia of the feet, bruxism, hemifacial spasm, tics and/or strabismus; segmental dystonia, Meige's syndrome, multifocal dystonias, hemidystonias, dopamine-responsive dystonias and Segawa dystonia.

In another particular aspect, this invention relates to a peptide of general formula (I), its stereoisomers, mixtures thereof, and/or its cosmetically or pharmaceutically acceptable salts, as described in this invention, for the treatment and/or care of the skin, preferably for the treatment and/or care of facial skin.

In another particular aspect, this treatment and/or care of the skin refers to the treatment and/or prevention of the signs of aging and/or photoaging.

In another particular aspect, this invention relates to a peptide of general formula (I), its stereoisomers, mixtures thereof, and/or its cosmetically or pharmaceutically acceptable salts, as described in this invention, for the treatment and/or care of skin affected by wrinkles and/or expressions lines.

Processes of Preparation

The synthesis of the peptides of the invention, their stereoisomers or their cosmetically or pharmaceutically acceptable salts can be performed according to conventional methods known in the prior art, such as methods of solid phase peptide synthesis [Stewart J. M. and Young J. D. (1984) "*Solid Phase Peptide Synthesis, 2nd edition*" Pierce Chemical Company, Rockford, Ill.; Bodanzsky M. and Bodanzsky A. (1984) "*The practice of Peptide Synthesis*" Springer Verlag, New Cork; Lloyd-Williams P., Albericio F. and Giralt E. (1997) "*Chemical Approaches to the Synthesis of Peptides and Proteins*" CRC, Boca Raton, Fla., USA], synthesis in solution, a combination of the methods for solid phase synthesis and solution synthesis or enzymatic synthesis [Kullmann W. (1980) "*Proteases as catalysts for enzymic syntheses of opioid peptides*" *J. Biol. Chem.* 255:8234-8238]. The peptides can also be obtained by fermentation of a bacterial strain, genetically engineered or not, in order to produce the desired sequences, by controlled hydrolysis of proteins of animal or vegetable origin, preferably vegetable origin, to release peptide fragments containing at least the desired sequence.

For example, a method of obtaining the peptides of the invention of formula (I) comprises the steps of:

coupling an amino acid with the N-terminal end protected and the C-terminal end free, onto an amino acid with the N-terminal end free and the C-terminal end protected or bound to a solid support;

removing the protective group of the N-terminal end;

repetition of the sequence of coupling and removal of the protective group of the N-terminal end until the desired peptidic sequence is obtained;

removal of the protective group of the C-terminal end or cleavage from the solid support.

Preferably, the C-terminal end is bound to a solid support and the process is conducted on solid phase and, therefore, includes the coupling of an amino acid with the N-terminal end protected and the C-terminal end free onto an amino acid with the N-terminal end free and the C-terminal end bound to a polymer support; removal of the protective group of the N-terminal end; and repetition of this sequence as many times as is necessary to obtain a peptide of the desired length, and finally followed by cleaving the synthesized peptide from the original polymer support.

The functional groups of the side chains of the amino acids are adequately protected with temporary or permanent protective groups throughout synthesis, and can be deprotected simultaneously or orthogonally to the process of cleaving the peptide from the polymer support.

Alternatively, solid phase synthesis can be carried out by a convergent strategy coupling a peptide onto the polymer support or onto an amino acid previously bound to the polymer support. Convergent synthesis strategies are widely known to the person skilled in the art and are described in Lloyd-Williams P., Albericio F. and Giralt E. in "*Convergent solid-phase peptide synthesis*" (1993) *Tetrahedron* 49:11065-11133.

The process can comprise the additional stages of deprotection of the N-terminal and C-terminal ends and/or cleavage of the peptide from the polymer support in a different order, using standard processes and conditions known in the prior art, after which the functional groups of these ends can be modified. The optional modification of the N-terminal and C-terminal ends can be carried out with the peptide of formula (I) bound to the polymeric support or once the peptide has been cleaved from the polymeric support.

Alternatively, $R_1$ may be introduced by the reaction of the N-terminal end of the peptide of the invention with a compound $R_1$-J, wherein $R_1$ is as described above and J is a leaving group for example, and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is $—OR_3$, $—NR_3R_4$ or $—SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the general formula (I) invention, wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric support.

A person skilled in the art would easily understand that the deprotection/cleavage steps of the C-terminal and N-terminal ends and their subsequent derivatization can be performed in a different order, according to the processes known in the prior art [Smith M. B. and March J. (1999) "*March's Advanced Organic Chemistry Reactions, Mechanisms and Structure*", 5th Edition, John Wiley & Sons, 2001].

The term "protective group" relates to a group which blocks a functional organic group and can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), Trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxocyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino)benzyl ester (Dmab), among others; preferred protective groups of the invention are the All, tBu, cHx, Bzl and Trt esters.

The side chains of the trifunctional amino acids can be protected during the synthetic process with temporary or permanent protective groups orthogonal to the protective groups of the N-terminal and C-terminal ends.

The guanidine group of the arginine side chain can be protected with the nitro group, allyloxycarbonyl (Alloc), para-toluenesulfonyl (tosyl, Tos), 2,2,5,7,8-pentamethylchroman-6-sulfonyl (Pmc), 2,2,4,6,7-pentamethyldihydrobenzofuran-5-sulfonyl (Pbf) or 4-methoxy-2,3,6-trimethylbenzenesulfonyl (Mtr), among others. The hydroxyl group of the tyrosine side chain can be protected with the 2-bromobenzyloxycarbonyl group (2-BrZ), tert-butyl (tBu), allyl (All), benzyl (Bzl) or 2,6-dichlorobenzyl (2,6-diClZ) among others. For the protection of amino group of the lysine side chain amides can used, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxocyclohexylidene)-3-methylbutyl (ivDde), or 1-(1-adamantyl)-1-methylethoxycarbonyl (Adpoc), among others. For the protection of the carboxyl group of the aspartic acid and glutamic acid side chains esters can be used, such as the tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others. The methionine side chain is protected with sulfoxide or is used unprotected.

In a preferred embodiment, the protective group strategy used is the strategy wherein the amino groups are protected by Boc, the carboxyl groups are protected by Bzl, cHx or All, the arginine side chain is protected with Tos, the lysine side chain is protected with CIZ, Fmoc or Alloc, the aspartic acid and glutamic acid side chain is protected with Bzl, cHx or All, the tyrosine side chain is protected with 2-BrZ or BzI and the methionine side chain is used unprotected.

In another preferred embodiment, the protective group strategy used is the strategy wherein the amino groups are protected by Fmoc, the carboxyl groups are protected by tBu, All or Trt, the arginine side chain is protected with Pbf or Pmc, the lysine side chain is protected with Boc or Mtt, the aspartic acid and glutamic acid side chain are protected with tBu or All, the tyrosine side chain is protected with tBu and the methionine side chain is used unprotected.

Examples of these and other additional protective groups, their introduction and removal, can be found in the literature [Greene T. W. and Wuts P. G. M., (1999) "*Protective groups in organic synthesis*" John Wiley & Sons, New York; Atherton B. and Sheppard R. C. (1989) "*Solid Phase Peptide Synthesis: A practical approach*" IRL Oxford University Press]. The term "protective groups" also includes the polymeric supports used in solid phase synthesis.

When synthesis takes place totally or partially on solid phase, the possible solid supports used in the method of the present invention involve polystyrene supports, polyethylene glycol grafted to polystyrene and similar, for example, and not restricted to, p-methylbenzhydrylamine (MBHA) resins [Matsueda G. R. and Stewart J. M. (1981) "*A p-methylbenzhydrylamine resin for improved solid-phase synthesis of peptide amides*" Peptides 2:45-50], 2-chlorotrityl resins [Barlos K., Gatos D., Kallitsis J., Papaphotiu G., Sotiriu P., Wenqing Y. and Schäfer W. (1989) "*Darstellung geschützter Peptid-Fragmente unter Einsatz substituierter Triphenylmethyl-Harze*" Tetrahedron Lett. 30:3943-3946; Barlos K., Gatos D., Kapolos S., Papaphotiu G., Schäfer W. and Wenqing Y. (1989) "Veresterung von partiell geschützten Peptid-*Fragmenten mit Harzen. Einsatz von 2-Chlortritylchlorid zur Synthese von Leu1-Gastrin I*" Tetrahedron Lett. 30:3947-3951], TentaGel® resins (Rapp Polymere GmbH), ChemMatrix® resins (Matrix Innovation, Inc) and similar, which may or may not include a labile linker, such as 5-(4-aminomethyl-3,5-dimethoxy phenoxy)valeric acid (PAL) [Albericio F., Kneib-Cordonier N., Biancalana S., Gera L., Masada R. I., Hudson D. and Barany G. (1990) "*Preparation* and *application of the* 5-(4-(9-*fluorenylmethyloxycarbonyl*)*aminomethyl*-3,5-*dimethoxy phenoxy*)*valeric acid* (*PAL*) *handle for the solid-phase synthesis of C-terminal peptide amides under mild conditions*" J. Org. Chem. 55:3730-3743], 2-[4-aminomethyl (2,4 dimethoxyphenyl)]phenoxyacetic acid (AM) [Rink H. (1987) "*Solid-phase synthesis of protected peptide fragments using a trialkoxy-diphenyl-methylester resin*" Tetrahedron Lett. 28:3787-3790], Wang [Wang S. S. (1973) "*p-Alkoxybenzyl Alcohol Resin* and *p-Alkoxybenzyloxycarbonylhydrazide Resin for Solid Phase Synthesis of Protected Peptide Fragments*" J. Am. Chem. Soc. 95:1328-1333] and similar, allowing the simultaneous deprotection and cleavage of the peptide from the polymeric support.

Cosmetic or Pharmaceutical Compositions

The peptides of the invention can be administered to inhibit AChR clustering by any means which produces the peptides' contact with their site of action in the body of a mammal, preferably a human being, and in the form of a composition that contains them.

To this regard, another aspect of the invention is a cosmetic or pharmaceutical composition which comprises at least a peptide of general formula (I), its stereoisomers, mixtures thereof, and/or its cosmetically or pharmaceutically acceptable salts together with at least one cosmetically or pharmaceutically acceptable adjuvant. These compositions can be prepared by conventional means known to persons skilled in the art ["*Harry's Cosmeticology*", Eight edition (2000) Rieger M. M., ed., New York Chemical Pub., NY, US; "*Remington: The Science and Practice of Pharmacy*", Twentieth edition (2003) Genaro A. R., ed., Lippincott Williams & Wilkins, Philadelphia, US].

The peptides of this invention have variable solubility in water, according to the nature of their sequence or any possible modifications in the N-terminal and/or C-terminal ends. Therefore, the peptides of this invention can be incorporated into the compositions by aqueous solution, and those which are not soluble in water can be solubilized in cosmetically or pharmaceutically acceptable conventional solvents for example, and not restricted to, ethanol, propanol, isopropanol, propylene glycol, glycerine, butylene glycol or polyethylene glycol or any combination thereof.

The cosmetically or pharmaceutically effective amount of the peptides of the invention which should be administered, as well as their dosage, will depend on numerous factors, including age, state of the patient, the nature or severity of the condition, disorder or disease to be treated, cared for or prevented, the route and frequency of administration and, in the particular, nature of the peptides to be used.

"Cosmetically and pharmaceutically effective amount" is understood to mean a non-toxic but sufficient amount of the peptide or peptides of the invention to provide the desired effect. The peptides of the invention are used in the cosmetic or pharmaceutical composition of this invention in cosmetically or pharmaceutically effective concentrations to achieve the desired effect; in a preferred form versus the total weight of the composition, between 0.00000001% (in weight) and 20% (in weight); preferably between 0.000001% (in weight) and 20% (in weight), more preferably between 0.0001% (in weight) and 10% (in weight) and even more preferably between 0.0001% (in weight) and 5% (in weight).

The peptides of the invention can also be incorporated into cosmetic or pharmaceutical delivery systems and/or sustained release systems.

The term "delivery systems" relates to a diluent, adjuvant, excipient or carrier with which the peptide of the invention is administered. These cosmetic or pharmaceutical carriers can be liquids, such as water, oils or surfactants, including those of petroleum, animal, vegetable or synthetic origin, for example, and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. In "*Remington's Pharmaceutical Sciences*" by E. W. Martin diluents, adjuvants or excipients are described as appropriate carriers.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems are liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, mixed micelles of surfactant-phospholipid, millispheres, microspheres and nanospheres, liposphere, millicapsules, microcapsules and nanocapsules, as well as microemulsions and nanoemulsions, which can be added to achieve a greater penetration of the active principle and/or improve its pharmacokinetic and pharmacodynamic properties. Preferred delivery or sustained release systems are liposomes, mixed micelles of surfactant-phospholipid and microemulsions, more preferably water-in-oil microemlusions with an internal structure of inverse micelle.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example, and not restricted to, orally or parenterally, including nasal, rectal, subcutaneous implantation or injection, or direct implantation or injection into a specific body part, and preferably should release a relatively constant quantity of the peptides of the invention. The amount of peptide contained in the sustained release system will depend, for example, on where the composition is to be administered, the kinetics and duration of the release of the peptide of the invention, as well as the nature of the condition, disorder and/or disease to be treated, cared for or prevented.

The peptides of this invention can also be adsorbed on solid organic polymers or solid mineral supports for example, and not restricted to, talc, bentonite, silica, starch or maltodextrin among others.

The compositions which contain the peptides of the invention can also be incorporated into fabrics, non-woven fabrics and medical devices which are in direct contact with the skin, thus releasing the peptides of the invention whether by biodegradation of the binding system to the fabric, non-woven fabric or medical device, or by the friction between them and the body, due to body moisture, the skin's pH or body temperature. Furthermore, the fabrics and non-woven fabrics can be used for making garments that are in direct contact with the body. Preferably, the fabrics, non-woven fabrics and medical devices containing the peptides of the invention are used for the treatment and/or care of those conditions, disorders and/or diseases that are a consequence of AChR clustering, preferably a consequence of muscle contraction.

Examples of fabrics, non-woven fabrics, garments, medical devices and means for immobilizing the peptides to them, among which are the delivery systems and/or the sustained release systems described above, can be found in literature and are known in the prior art [Schaab C. K. (1986) "*Impregnating Fabrics With Microcapsules*", *HAPPI* May 1986; Nelson G. (2002) "*Application of microencapsulation in textiles*" *Int. J. Pharm.* 242:55-62; "*Biofunctional Textiles and the Skin*" (2006) *Curr. Probl. Dermatol.* v.33, Hipler U. C. and Elsner P., eds. S. Karger A G, Basel, Switzerland; Malcom R. K.; McCullagh S. D., Woolfson A. D., Gorman S. P., Jones D. S. and Cuddy J. (2004) "*Controlled release of a model antibacterial drug from a novel self-lubricating silicone biomaterial*" *J. Cont. Release* 97:313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the peptides of this invention, their stereoisomers, mixtures thereof and/or their cosmetically or pharmaceutically acceptable salts, can be used in different types of compositions of topical or transdermal application, optionally including cosmetically or pharmaceutically acceptable excipients necessary for formulating the desired administration form [Fauli i Trillo C. (1993) in "Tratado de Farmacia Galénica" Luzán 5, S. A. Ediciones, Madrid].

The compositions of topical or transdermal application can be produced in any solid, liquid or semisolid formulation, for example, and not restricted to, creams, multiple emulsions for example, and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories for example, and not restricted to bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks; or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic and pharmaceutical compositions of the invention may include agents which increase the percutaneous absorption of the peptides of this invention, for example, and not restricted to, dimethylsulfoxide, dimethylacetamide, dimethylformamide, surfactants, azone (1-dodecylazacycloheptan-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the cosmetic or pharmaceutical compositions containing the peptides of this invention, their stereoisomers and/or their cosmetically or pharmaceutically acceptable salts can be used in different types of formulations for oral administration, preferably in the form of oral cosmetics or drugs, for example, and not restricted to, capsules, including gelatin capsules, soft capsules, hard capsules, tablets, including sugar coated tablets, powders, granules, chewing gum, solutions, suspensions, emulsions, syrups, polysaccharide films, jellies or gelatins, and any other form known by the person skilled in the art. In particular, the peptides of the invention can be incorporated into any form of functional food or fortified food, for example, and not restricted to, dietary bars or compact or non-compact powders. These powders can be dissolved in water, soda, dairy products, soybean derivatives or can be incorporated into dietary bars. The peptides of this invention can be formulated with common excipients and adjuvants for oral compositions or food supplements, for example, and not restricted to, fat components, aqueous components, humectants, preservatives, texturizing agents, flavors, aromas, antioxidants and colorants common in the food industry.

Cosmetic or pharmaceutical compositions containing the peptides of the invention, their stereoisomers, mixtures thereof and/or their cosmetically or pharmaceutically acceptable salts can also be administered by topical or transdermal route, as well as by any other appropriate route, as for example oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal route, subcutaneous, intradermal, intravascular injections, such as intravenous, intramuscular, intraocular, intravitreal, intracorneal, intraspinal, intramedullary nailing, intracraneal, intracervical, intracerebral, intrameningeal, intraarticular, intrahepatic, intrathoracic, intratracheal, intrathecal and intraperitoneal, and any another similar injection or infusion technique. A review of the different pharmaceutical forms of administration of the active ingredients and excipients necessary for obtaining them can be found, for example, in the "Tratado de Farmacia Galénica" C. Fault i Trillo, 1993, Luzán 5, S. A. Ediciones, Madrid.

Among the cosmetically or pharmaceutically acceptable adjuvants contained in the cosmetic or pharmaceutical compositions described in this invention include additional ingredients commonly used in compositions for the treatment and/or care of the skin for example, and not restricted to, other agents inhibiting AChR clustering, other agents inhibiting muscle contraction, anticholinergic agents, elastase inhibiting agents, matrix metalloproteinases inhibiting agents, melanin synthesis stimulating or inhibiting agents, whitening or depigmenting agents, pro-pigmenting agents, self-tanning agents, anti-aging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiemetic agents, antiviral agents, antiparasitic agents, emulsifiers, emollients, organic solvents, liquid propellants, skin conditioners such as humectants, substances that retain moisture, alpha hydroxyacids, beta hydroxyacids, moisturizers, epidermal hydrolytic enzymes, vitamins, pigments or colorants, dyes, gelling polymers, thickeners, surfactants, softening agents, anti-wrinkle agents, agents able to reduce or treat bags under the eyes, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, such as collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, aquaporin synthesis-stimulation agents, hyaluronic acid synthesis-stimulating agents, fibronectin synthesis-stimulating agents, sirtuin synthesis-stimulating agents, agents stimulating the synthesis of lipids and components of the stratum corneum (ceramides, fatty acids, etc.), agents that inhibit collagen degradation, other agents that inhibit elastin degradation, agents that inhibit serine proteases such as cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, antihyperkeratosis agents, comedolytic agents, antipsoriasis agents, DNA repair agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents and/or analgesics, anesthetic agents, agents acting on capillary circulation and/or microcirculation, agents stimulating angiogenesis, agents that inhibit vascular permeability, venotonic agents, agents acting on cell metabolism, agents to improve the dermal-epidermal junction, agents inducing hair growth, hair growth inhibiting or retardant agents, preservatives, perfumes, chelating agents, vegetable extracts, essential oils, marine extracts, agents obtained from a biofermentation process, mineral salts, cell extracts and sunscreens (active organic or mineral photoprotective agents against ultraviolet A and/or B rays) among others, provided they are physically and chemically compatible with the other components of the composition and especially with the peptides of general formula (I) contained in the composition of this invention. Furthermore, the nature of these additional ingredients should not unacceptably alter the benefits of the peptides of this invention. The nature of these additional ingredients can be synthetic or natural, such as vegetable extracts, or obtained from a biotechnological process or obtained from a combination of a synthetic process and a biotechnological process. Additional examples can be found in the *CTFA International Cosmetic Ingredient Dictionary & Handbook,* 12th Edition (2008). In the context of this invention, biotechnological process is understood to be any process which produces the active principal, or part of it, in an organism, or in a part of it.

An additional aspect of this invention relates to a cosmetic or pharmaceutical composition containing a cosmetically or pharmaceutically effective amount of at least one peptide according to the general formula (I), its stereoisomers, mixtures thereof and/or its cosmetically or pharmaceutically acceptable salts, and also a cosmetically or pharmaceutically effective amount of at least one extract which is an anti-wrinkle agent and/or anti-aging agent for example, and not restricted to, the extracts *Vitis vinifera, Rosa canina, Curcuma longa, Iris pallida, Theobroma cacao, Ginkgo biloba, Leontopodium Alpinum* or *Dunaliella salina* among others, or at least a synthetic compound or bio-fermentation product which is an anti-wrinkle agent and/or anti-aging agent for example, and not restricted to, Matrixyl® [INCI: Palmitoyl Pentapeptide-4], Matrixyl 3000® [INCI: Palmitoyl Tetrapeptide-7, Palmitoyl Oligopeptide], Essenskin™ [INCI: calcium hydroxymethionine], Renovage [INCI: teprenone] or Dermaxyl® [INCI: Palmitoyl Oligopeptide] marketed by Sederma, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia Siliqua*) Gum] or Preregen® [INCI: *Glycine Soja* (Soybean) Protein, Oxido Reductases] marketed by Pentapharm/DSM, Myoxinol™ [INCI: Hydrolyzed Hibiscus Esculentus Extract], Syniorage™ [INCI: Acetyl Tetrapeptide-11], Dermican™ [INCI: Acetyl Tetrapeptide-9] or DN-AGE™ LS [INCI: *Cassia Alata* leaf Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Aldenine® [INCI: Hydrolized wheat protein, hydrolized soy protein, Tripeptide-1], Preventhelia™ [INCI: Diaminopropionoyl Tripeptide-33], Decorinyl™ [INCI: Tripeptide-10 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Lipochroman-6 [INCI: Dimethylmethoxy Chromanol], Chromabright™ [INCI: Dimethylmethoxy Chromanyl Palmitate], Antarcticine® [INCI: Pseudoalteromonas Ferment Extract], Vilastene™ [INCI: Lysine HCl, Lecithin, Tripeptide-10 Citrulline,], acetyl-arginyl-phenylglycyl-tryptophyl-phenylglycine, acetyl-arginyl-phenylglycyl-valyl-glycine or acetyl-arginyl-phenylglycyl-valyl-phenylglycine marketed by, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza Sativa* (Rice) Extract], D'Orientine™ IS [INCI: *Phoenix Dactylifera* (Date) Seed Extract], Phytoquintescine™ [INCI: Einkorn (*Triticum Monococcum*) Extract] or Quintescine™ IS [INCI: Dipeptide-4] marketed by Vincience/ISP, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: Spilanthes *Acmella* Flower Extract] or Gatuline® Age Defense 2 [INCI: *Juglans Regia* (Walnut) Seed Extract] marketed by Gattefosse, Thalassine™ [INCI: *Algae* Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: *Pyrus Malus* Fruit Extract, *Glycine Soja* Seed Extract] or Juvenesce [INCI: Ethoxydiglicol and Caprylic Triglycerid, Retinol, Ursolic Acid, Phytonadione, Ilomastat] marketed by Coletica, Ameliox [INCI: Carnosine, Tocopherol, Silybum Marianum Fruit Extract] or PhytoCellTec *Malus Domestica* [INCI: *Malus Domestica* Fruit Cell Culture] marketed by Mibelle Biochemistry, Bioxilift [INCI: Pimpinella Anisum Extract] or SMS Anti-Wrinkle® [INCI: Annona *Squamosa* Seed Extract] marketed by Silab, antagonists of the $Ca^{2+}$ channel for example, and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes for example, and not restricted to, photolyase or T4 endonuclease V, or chloride channel agonists among others.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and in addition, a pharmaceutically effective amount of at least one extract which is an agent inhibiting AChR clustering and/or muscle contraction inhibiting agent and/or anticholinergic agent for example, and not restricted to, the extracts of *Atropa belladonna, Hyoscyamus niger, Mandragora officinarum, Chondodendron tomentosum*, plants of the *Brugmansia* genus, or *Datura* genus among others and or at least one synthetic compound or bio-fermentation product which is an agent inhibiting AChR clustering and/or muscle contraction inhibiting agent and/or anticholinergic agent for example, and not restricted to *Clostridium botulinum* toxin, peptides derived from SNAP-25 protein, baclofen, carbidopa, levodopa, bromocriptine, chlorphenesin, chlorzoxazone, donepezil, mephenoxalone, reserpine, tetrabenazine, dantrolene, thiocolchicoside, tizanidine, clonidine, procyclidine, glycopyrrolate, atropine, hyoscyamine, benztropine, scopolamine, promethazine, diphenhydramine, dimenhydrinate, dicyclomine, cyclobenzaprine, orphenadrine, flavoxate, cyclopentolate, ipratropium, oxybutynin, pirenzepine, tiotropium, trihexyphenidyl, tolterodine, tropicamide, solifenacin, darifenacin, mebeverine, trimethaphan, atracurium, cisatracurium, doxacurium, fazadinium, metocurine, mivacurium, pancuronium, pipecuronium, rapacuronium, tubocurarine, dimethyl tubocurarine, rocuronium, vecuronium, suxamethonium, 18-methoxycoronaridine, carisoprodol, febarbamate, meprobamate, metocarbamol, phenprobamate, tibamate, anticonvulsant agents such as levetiracetam, stiripentol, phenobarbital, methylphenobarbital, pentobarbital, metharbital, barbexaclone, primidone, carbamazepine, oxcarbazepine, benzodiazepines for example, and not restricted to, clonazepam, cloxazolam, clorazepate, diazepam, flutoprazepam, lorazepam, midazolam, nitrazepam, nimetazepam, phenazepam, temazepam, tetrazepam or clobazam among others.

An additional aspect of this invention relates to a pharmaceutical composition which comprises a pharmaceutically effective amount of at least one peptide according to the general formula (I), its stereoisomers, mixtures thereof and/or its pharmaceutically acceptable salts, and a pharmaceutically effective amount of at least one natural extract or essential oil which is an anti-inflammatory agent and/or analgesic for example, and not restricted to, madecassoside, echinacea, amaranth oil, sandalwood oil, peach leaf extract, Aloe vera extract, *Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officialis, Salix alba, Silybum marianum, Tanacetum parthenium, Thymus vulgaris, Uncaria guianensis or Vaccinum myrtillus* among others or at least one synthetic compound or bio-fermentation product which is an anti-inflammatory agent and/or analgesic for example, and not restricted to, mometasone furoate and prednisolone, nonsteroidal anti-inflammatory drugs including cyclooxygenase or lipoxygenase inhibitors, benzydamine, acetylsalicylic acid, rosmarinic acid, ursolic acid, derivatives of glycyrrhizinate, α-bisabolol, azulene and analogues, sericoside, ruscogenin, escin, scoline, rutin and analogues, hydrocortisone, clobetasol, dexamethasone, prednisone, paracetamol, amoxiprin, benorilate, choline salicylate, diflunisal, faislamine, methyl salicylate, magnesium salicylate, salsalate, diclofenac, aceclofenac, acemetacin, bromfenac, etodolac, indometacin, oxametacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizol, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone; morphine, codein, oxycodone, hydrocodone, diamorphine, pethidine, tramadol, buprenorphine, benzocaine, lidocaine, chloroprocaine, tetracaine, procaine, tricyclic antidepressants, amitriptyline, carbamazepine, gabapentin, pregabalin, pantenol, biotin, disodium lauriminodipropionate tocopheryl phosphate, ciclopirox olamine, nordihydroguaiaretic acid, Neutrazen™ [INCI: Water, Butylene Glycol, Dextran, Palmitoyl Tripeptide-8] marketed by Atrium Innovations/Unipex Group, Meliprene® [INCI: Dextran, Acetil Heptapeptide-1] marketed by Institut Européen de Biologie Cellulaire/Unipex Group, Skinasensyl™ [INCI: Acetyl Tetrapeptide-15] marketed by Laboratoires Sérobiologiques/Cognis, coenzyme Q10 or alkyl glyceryl ethers among others.

Applications

Another aspect of this invention relates to the use of at least one of the peptides of general formula (I), its stereoisomers, mixtures thereof and/or its cosmetically or pharmaceutically acceptable salts in the preparation of a cosmetic or pharmaceutical composition for the treatment and/or care of those conditions, disorders and/or diseases which are a consequence of muscle contraction, preferably a consequence of acetylcholine receptor clustering.

Another aspect of this invention relates to the use of at least one of the peptides of general formula (I), its stereoisomers, mixtures thereof and/or its cosmetically or pharmaceutically acceptable salts in the preparation of a cosmetic or pharmaceutical composition for the inhibition of muscle contraction, preferably for the inhibition of acetylcholine receptor clustering.

Preferably, among the disorders and/or diseases to be treated which are caused by muscle contraction are dystonias, and more particularly focal dystonia for example, and not restricted to, blepharospasm, torsion dystonia, cervical dystonia or torticollis, laryngeal dystonia or spasmodic dysphonia, oromandibular dystonia, dystonia of limbs such as writer's or musician's cramp or dystonia of the feet, bruxism, hemifacial spasm, tics and/or strabismus; segmental dystonia, Meige's syndrome, multifocal dystonias, hemidystonias, dopamine-responsive dystonias and Segawa dystonia.

Another aspect of this invention relates to the use of at least one of the peptides of general formula (I), its stereoisomers, mixtures thereof and/or its cosmetically or pharmaceutically acceptable salts in the preparation of a cosmetic or pharmaceutical composition for the treatment and/or care of skin, preferably facial skin.

According to a preferred embodiment, the treatment and/or care of the skin is a treatment and/or prevention of the signs of aging and/or photoaging.

According to another preferred embodiment, this invention relates to the use of at least one of the peptides of general formula (I), its stereoisomers, mixtures thereof and/or its cosmetically or pharmaceutically acceptable salts in the preparation of a cosmetic or pharmaceutical composition for the treatment and/or care of skin affected by wrinkles and/or expression lines.

Examples of cosmetic or pharmaceutical compositions for the treatment and/or care of the skin and/or body include creams, multiple emulsions for example, and not restricted to, oil and/or silicone in water emulsions, water in oil and/or silicone emulsions, water/oil/water or water/silicone/water type emulsions and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, liniments, sera, soaps, shampoos, conditioners, serums, polysaccharide films, ointments, mousses, pomades, powders, bars, pencils and sprays or aerosols (sprays), including leave-on and rinse-off formulations, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, make-up products such as make-up foundation, for example fluid foundation and compact foundation, make-up removal lotions, make-up removal milks, under-eye concealers, eye shadows, lipsticks, lip protectors, lip gloss and powders, among others.

The compositions containing the peptides of this invention can be applied to the skin or can be administered orally or parenterally as necessary to treat and/or care for a condition, disorder and/or disease.

The cosmetic or pharmaceutical compositions of this invention can be applied to the skin by iontophoresis, sonophoresis, electroporation, microelectric patches, mechanical pressure, osmotic pressure gradient, occlusive cure, microinjections, needle-free injections by means of pressure, such as injections by oxygen pressure, or any combination thereof, to achieve a greater penetration of the peptide of the invention.

An additional aspect of this invention relates to a method of treatment and/or care of those conditions, disorders and/or diseases of mammals, preferably humans, which are a consequence of muscle contraction, preferably a consequence of AChR clustering, which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing them.

Another aspect of this invention relates to method of treatment and/or care of those conditions, disorders and/or diseases of mammals, preferably humans, which inhibit muscle contraction, preferably inhibit acetylcholine receptor clustering, which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing them.

According to a particular embodiment the disorders and/or diseases to be treated are selected from the group of dystonias, and more particularly focal dystonia for example, and not restricted to, blepharospasm, torsion dystonia, cervical dystonia or torticollis, laryngeal dystonia or spasmodic dysphonia, oromandibular dystonia, dystonia of limbs such as writer's or musician's cramp or dystonia of the feet, bruxism, hemifacial spasm, tics and/or strabismus; segmental dystonia, Meige's syndrome, multifocal dystonias, hemidystonias, dopamine-responsive dystonias and Segawa dystonia.

Another aspect of this invention provides a method of treatment and/or care of the skin, preferably facial skin, which comprises administering a cosmetically or pharmaceutically effective amount of at least one peptide of general formula (I), its stereoisomers, mixtures thereof and/or its cosmetically or pharmaceutically acceptable salts, preferably in the form of a cosmetic or a pharmaceutical composition containing them.

According to a particular embodiment, the treatment and/or care of the skin is a treatment and/or prevention of the signs of aging and/or photoaging of the skin.

According to another particular embodiment, this invention provides a method for the treatment and/or care of skin affected by wrinkles and/or expression lines which comprises administering a cosmetically or pharmaceutically effective amount of at least one peptide of general formula (I), its stereoisomers, mixtures thereof and/or its cosmetically or pharmaceutically acceptable salts, preferably in the form of a cosmetically or a pharmaceutically composition containing them.

According to another particular embodiment, this invention provides a method of treatment and/or care of those conditions, disorders and/or diseases which are a consequence of muscle contraction, which comprises the topical or transdermal application onto the skin or oral or parental administration of a cosmetic or pharmaceutical composition containing at least one peptide of the invention, its stereoisomers, mixtures thereof and/or its cosmetic or pharmaceutical acceptable salts.

In another particular aspect, the treatment and/or care of this invention is carried out by topical or transdermal application, preferably, the topical or transdermal application is carried out by iontophoresis, sonophoresis, electroporation, mechanical pressure, osmotic pressure gradient, occlusive cure, microinjections, needle-free injections by means of pressure, microelectric patches or any combination thereof.

In another particular aspect, the treatment and/or care is carried out by oral administration.

In another particular aspect, the treatment and/or care is performed by parenteral application.

The frequency of application or administration can vary greatly, depending on the needs of each subject and the seriousness of the condition, disorder or disease to be treated or cared for, with a recommendation of an application or administration range from once a month to ten times a day, preferably from once a week to four times a day, more preferably from three times a week to three times a day, even more preferably once or twice a day.

The following specific examples provided here illustrate the nature of this invention. These examples are included for illustrative purposes only and should not be construed as limitations on the invention claimed herein.

EXAMPLES

General Methodology

All reagents and solvents are of synthesis quality and are used without additional treatment.

Abbreviations

The abbreviations used for amino acids follow the IUPAC-IUB Joint Commission on Biochemical Nomenclature rules outlined in *Eur. J. Biochem.* (1984) 138:9-37 and in *J. Biol. Chem.* (1989) 264:633-673.

®, resin; 2,6-diClZ, 2,6-dichlorobenzyl; 2-BrZ, 2-bromobenzyloxycarbonyl; Ac, acetyl; ACh, acetylcholine; AChRs, acetylcholine receptors; Adpoc, 1-(1-adamantyl)-1-methyl ethoxycarbonyl; All, allyl; Alloc, allyloxycarbonyl; AM, 2-[4-aminomethyl -(2,4-dimethoxyphenyl)]phenoxyacetic acid; DNA, deoxyribonucleic acid; Arg, arginine; Asp, aspartic acid; Boc, tert-butyloxycarbonyl; Bzl, benzyl; CbZ, benzyloxycarbonyl; cHx, cyclohexyl; ClTrt-®, 2-chlorotrityl resin; ClZ, 2-chlorobenzyl; cps, centipoise; C-terminal, carboxy-terminal; DCM, dichloromethane; Dde, N-[1-(4,4-dimethyl-2,6-dioxocyclohex-1-ylidene)ethyl; DIEA, N,N-diisopropylethylamine; DIPCDI, N,N'-diisopropylcarbodiimide; Dmab, 4-(N-[1-(4,4-dimethyl-2,6-dioxocyclohexylidene)-3-methylbutyl]amino)benzyl; DMF, N,N-dimethylformamide; DMSO, dimethyl sulfoxide; Dnp, 2,4-dinitrophenol; DPPC, dipalmitoylphosphatidylcholine; EDTA, ethylenediaminetetraacetic acid; equiv, equivalent; ES-MS, electrospray ionization mass spectrometry; Fm, fluorenylmethyl; Fmoc, 9-fluorenylmethyloxycarbonyl; Glu, glutamic acid; HOAt, 1-hydroxyazabenzotriazole; HOBt, 1-hydroxybenzotriazole; HPLC, high performance liquid chromatography; INCI, International Nomenclature of Cosmetic Ingredients; ivDde, 1-(4,4-dimethyl-2,6-dioxocyclohexylidene)-3-methyl-butyl; Leu, leucine; Lys, lysine; mAChR, muscarinic acetylcholine receptors; MASC, MuSK-accessory specificity component; MBHA, p-methylbenzhydrylamine; MeCN, acetonitrile; MeOH, methanol; Met, methionine; MLV, multilaminar vesicles; Mtr, 4-methoxy-2,3,6-trimethylbenzenesulfonyl; Mtt, methoxytrityl or methyltrityl; MuSK, muscle specific kinase; nAChR, nicotinic acetylcholine receptors; NMJ, neuromuscular junction; N-terminal, amino-terminal; PAL, 5-(4-aminomethyl-3,5-dimethoxyphenoxy) valeric acid; Palm, palmitoyl; Pbf, 2,2,4,6,7-pentamethyldihydrobenzofuran-5-sulfonyl; PBS, phosphate buffered saline; Phe, phenylalanine; Pmc, 2,2,5,7,8-pentamethylchroman-6-sulfonyl; pNZ, p-nitrobenzyloxycarbonyl; Pro, proline; q.s., quantity sufficient; q.s.p., quantity sufficient for; RATL, rapsyn-associated transmembrane linking molecule; SNARE, soluble NSF attachment protein receptors; tBu, tert-butyl; Teoc, 2-(trimethylsilyl)ethyloxycarbonyl; TFA, trifluoroacetic acid; THF, tetrahydrofuran; TIS, triisopropylsilane; Tos, p-toluenesulfonyl or tosyl; Troc, 2,2,2-trichloroethyloxycarbonyl; Trt, trityl; Tyr, tyrosine; ULV, unilaminar vesicles; UV, ultraviolet; Z, benzyloxycarbonyl.

Chemical Synthesis

All synthetic processes were carried out in polypropylene syringes fitted with porous polyethylene discs or Pyrex® reactors fitted with porous plates. Solvents and soluble reagents were removed by suction. The Fmoc group was removed with piperidine-DMF (2:8, v/v) (1×1 min, 1×5 min, 5 mL/g resin) [Lloyd-Williams P., Albericio F. and Giralt E. (1997) *"Chemical Approaches to the Synthesis of Peptides and Proteins"* CRC, Boca Raton, Fla., USA]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin trial [Kaiser E., Colescott R. L., Bossinger C. D. and Cook P. I. (1970) *"Color test for detection of free terminal amino groups in the solid-phase synthesis of peptides"* Anal. Biochem. 34:595-598] or chloranil trial [Christensen T. (1979) *"A qualitative test for monitoring coupling completeness in solid-phase peptide synthesis using chloranil"* Acta Chem. Scand. 33B:763-766]. All synthetic reactions and washes were carried out at room temperature.

HPLC chromatographic analysis was carried out with Shimadzu equipment (Kyoto, Japan) using a reversed-phase column thermostatized at 30° C. (250×4.0 mm, Kromasil $C_8$, 5 µm, Akzo Nobel, Sweden). The elution was carried out using a gradient of acetonitrile (+0.07% TFA) in water (+0.1% TFA) at a flow rate of 1 mL/min and detection was carried out at 220 nm.

Example 1

Prophetic

Obtaining Fmoc-$W_n$-$X_m$-$AA_1$-$AA_2$-$AA_3$-$AA_4$-$AA_5$-$AA_6$-$Y_p$-$Z_s$-O-2-ClTrt-®, wherein $AA_1$ is -L-Asp-, -L-Gluor -L-Pro-; $AA_2$ is -L-Asp-; $AA_3$ is -L-Tyr- or -L-Arg-; $AA_4$ is -L-Phe- or -L-Tyr-; $AA_5$ is -L-Arg- or -L-Lys-; $AA_6$ is -L-Leu- or -L-Met-; y n, m, p and s are 0. 3.11 g of Fmoc-L-Leu-OH or 3.27 g of Fmoc-L-Met-OH (8.8 mmol; 1 equiv) dissolved in 55 mL of DCM to which is added 1.3 mL of DIEA (7.6 mmol; 0.86 equiv) are coupled onto the dry 2-chlorotrityl (5.5 g; 8.8 mmol). They are stirred for 5 min, after which 2.5 mL of DIEA are added (14.6 mmol; 1.66 equiv). The mixture is allowed to react for 40 min. The remaining chloride groups are blocked by treatment with 4.4 mL of MeOH.

The N-terminal Fmoc group is deprotected as described in the general methods and 14.27 g of Fmoc-L-Arg(Pbf)-OH or 10.31 g of Fmoc-L-Lys(Boc)-OH (22 mmol; 2.5 equiv) are coupled onto the peptidyl resin in the presence of DIPCDI (3.39 mL; 22 mmol; 2.5 equiv) and HOBt (3.37 g; 22 mmol; 2.5 equiv) using DMF as a solvent for 1 hour. The resin is then washed as described in the general methods and the deprotection treatment of the Fmoc group is repeated to couple onto the next amino acid. Following the protocols described the following is sequentially coupled: 8.52 g of Fmoc-L-Phe-OH or 10.11 g of Fmoc-L-Tyr(tBu)-OH (22 mmol; 2.5 equiv); 14.27 g of Fmoc-L-Arg(Pbf)-OH or 10.11 g of Fmoc-L-Tyr (tBu)-OH (22 mmol; 2.5 equiv); 9.05 g of Fmoc-L-Asp (OtBu)-OH (22 mmol; 2.5 equiv) and subsequently 7.43 g of Fmoc-L-Pro-OH, 9.75 g of Fmoc-L-Glu(OtBu)-OH or 9.05 g of Fmoc-L-Asp(OtBu)-OH (22 mmol; 2.5 equiv) in the presence in each coupling of 3.37 g of HOBt (22 mmol; 2.5 equiv) and 3.39 mL of DIPCDI (22 mmol; 2.5 equiv).

After the synthesis, the peptidyl resins are washed with DCM (5×3 min) and dried by nitrogen stream.

Example 2

Obtaining Fmoc-$W_n$-$X_m$-$AA_1$-$AA_2$-$AA_3$-$AA_4$-$AA_5$-$AA_6$-$Y_p$-$Z_s$-AM-MBHA-®, wherein $AA_1$ is -L-Asp-, -L-Glu- or -L-Pro-; $AA_2$ is -L-Asp-; $AA_3$ is -L-Tyr- or -L-Arg-; $AA_4$ is -L-Phe- or -L-Tyr-; $AA_5$ is -L-Arg- or -L-Lys-; $AA_6$ is -L-Leu- or -L-Met-; and n, m, p and s are 0.

Weights have been normalized. 6.85 g of the Fmoc-AM-MBHA resin with a functionalization of 0.73 mmol/g (5 mmol) were treated with piperidine-DMF according to the described general protocol in order to remove the Fmoc group. 8.84 g of Fmoc-L-Leu-OH or 9.29 g of Fmoc-L-Met-OH (25 mmol; 5 equiv) were incorporated onto the deprotected resin in the presence of DIPCDI (3.85 mL, 25 mmol; 5 equiv) and HOBt (3.85 g, 25 mmol; 5 equiv) using DMF as a solvent for 1 hour.

The resin was then washed as described in the general methods and the deprotection treatment of the Fmoc group was repeated to couple the next amino acid. Following the previously described protocols 11.72 g of Fmoc-L-Lys(Boc)-OH or 16.22 g of Fmoc-L-Arg(Pbf)-OH (25 mmol; 5 equiv); 11.49 g of Fmoc-L-Tyr(tBu)-OH or 9.69 g of Fmoc-L-Phe-OH (25 mmol; 5 equiv); 11.49 g of Fmoc-L-Tyr(tBu)-OH or 16.22 g of Fmoc-L-Arg(Pbf)-OH (25 mmol; 5 equiv); 10.29 g of Fmoc-L-Asp(OtBu)-OH (25 mmol; equiv); and subsequently 8.44 g of Fmoc-L-Pro-OH, 10.29 g of Fmoc-L-Asp (OtBu)-OH or 11.09 g of Fmoc-L-Glu(OtBu)-OH (25 mmol; 5 equiv) were coupled sequentially each coupling in the presence of 3.85 g of HOBt (25 mmol; 5 equiv) and 3.85 mL of DIPCDI (25 mmol; 5 equiv).

After the synthesis, the peptidyl resins were washed with DCM (5×3 min) and dried by nitrogen stream.

Example 3

General Process for Removal of Fmoc N-Terminal Protective Group

The N-terminal Fmoc group of the peptidyl resins obtained in Example 2 was deprotected as described in the general methods (20% piperidine in DMF, 1×5 min+1×20 min). The peptidyl resins were washed with DMF (5×1 min), DCM (4×1 min), diethyl ether (4×1 min) and dried under vacuum. The same process could have been applied to the N-terminal Fmoc group of the peptidyl resins obtained in prophetic Example 1.

Example 4

Process for Introducing the $R_1$ Palmitoyl Group onto the Peptidyl Resins Obtained in Example 3

Weights have been normalized. 2.56 g of palmitic acid (10 mmol; 10 equiv) pre-dissolved in DMF (1 mL) were added onto 1 mmol of the peptidyl resins obtained in Example 3, in the presence of 1.53 g of HOBt (10 mmol; 10 equiv) and 1.54 mL of DIPCDI (10 mmol; 10 equiv). They were allowed to react for 15 hours, after which the resins were washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and were dried under vacuum.

Example 5

Process for Introducing the R, Acetyl Group onto the Peptidyl Resins Obtained in Example 3

Weights have been normalized. 1 mmol of the peptidyl resins obtained in Example 3 was treated with 25 equiv of acetic anhydride in the presence of 25 equiv of DIEA using 5 mL of DMF as a solvent. They were allowed to react for 30 mins, after which the peptidyl resins were washed with DMF (5×1 min), DCM (4×1 min), diethyl ether (4×1 min) and were dried under vacuum.

Example 6

Cleavage Process from the Polymeric Support of the Peptidyl Resins Obtained in Examples 3, 4 and 5

Weights have been normalized. 200 mg of the dried peptidyl resins obtained in Examples 4 and 5 were treated with 5 mL of TFA:TIS:$H_2O$ (90:5:5) for 2 hours at room temperature under stirring. Filtrates were collected onto 50 mL cold diethyl ether, they were filtered through polypropylene syringes fitted with porous polyethylene discs and washed 5 times with 50 mL diethyl ether. The final precipitates were dried under vacuum.

HPLC analysis of the obtained peptides in gradients of MeCN (+0.07% TFA) in $H_2O$ (+0.1% TFA) showed a purity exceeding 80% in all cases. The identity of the peptides obtained was confirmed by ES-MS. The same process could have been applied to the peptidyl resins obtained in Example 3.

Example 7

Prophetic

Cleavage process of the polymeric support and functionalization with $R_2$ substituted amine: Obtaining: Ac-$W_n$-$X_m$-$AA_1$-$AA_2$-$AA_3$-$AA_4$-$AA_5$-$AA_6$-$Y_p$-$Z_s$-NH—$(CH_2)_{15}$—$CH_3$, wherein $AA_6$ is -L-Leu- or -L-Met-; $AA_5$ is -L-Arg- or -L-Lys-; $AA_4$ is -L-Phe- or -L-Tyr-; $AA_3$ is -L-Tyr- or -L-Arg-; $AA_2$ is -L-Asp-; $AA_1$ is -L-Asp-, -L-Glu- or -L-Pro-; and n, m, p and s are 0.

The peptides Ac-W$_n$-X$_m$-AA$_1$-AA$_2$-AA$_3$-AA$_4$-AA$_5$-AA$_6$-Y$_p$-Z$_s$-OH with fully protected side chains are obtained by treating 150 mg of the peptidyl resins Ac-W$_n$-X$_m$-AA$_1$-AA$_2$-AA$_3$-AA$_4$-AA$_5$-AA$_6$-Y$_p$-Z$_s$-O-2-ClTrt-® of Example 5, previously desiccated under vacuum in the presence of KOH, with 3 mL of a 3% solution of TFA in DCM for 5 min. The filtrates are collected onto 50 mL of cold diethyl ether and the treatment is repeated three times. Ethereal solutions are evaporated to dryness at reduced pressure and room temperature, the precipitates are redissolved in 50% MeCN in H$_2$O and lyophilized. 10 mg of the obtained crude peptides are weighed in a flask and 3 equiv of hexadecylamine and 25 mL of anhydrous DMF are added. 2 equiv of DIPCDI are added, and left to react being magnetically stirred at 47° C. The reactions are monitored by HPLC until disappearance of the initial products, which are complete after 24-48 hours. The solvents are evaporated to dryness and co-evaporated twice with DCM. The obtained residues [Ac-W$_n$-X$_m$-AA$_1$-AA$_2$-AA$_3$-AA$_4$-AA$_5$-AA$_6$-Y$_p$-Z$_s$-NH—(CH$_2$)$_{15}$—CH$_3$ with fully protected side chains] are redissolved in 25 mL of a mixture of TFA:DCM:anisole (49:49:2) and left to react for 30 min at room temperature. 250 mL of cold diethyl ether are added, the solvents are evaporated under reduced pressure and two additional co-evaporations with ether are carried out. The residues are dissolved in a mixture of 50% MeCN in H$_2$O and lyophilized.

HPLC analysis of the obtained peptides in gradients of MeCN (+0.07% TFA) in H$_2$O (+0.1% TFA) showed a purity exceeding 60% in all cases.

Example 8

A ChR Clustering Inhibition Trial

The peptides were resuspended in water in the presence of 0.5% DMSO. $10^4$ mouse myoblasts were seeded in a 12-well plate and cultured in differentiation medium for 4-6 days until myotubes formed. The differentiation medium was removed and the cells were incubated for 16 hours with 5M NaCl, after which the medium was removed and the cells were incubated with the peptides at 0.1 mM for 24 hours. After this period, 5 μg/mL of the C-terminal agrin fragment dissolved in PBS (+0.1% BSA) were added and were incubated for 5 hours at 37° C.

The cells were fixed and an immunocytochemistry was performed with α-bungarotoxin conjugated to tetramethylrhodamine to visualize the AChRs. The myotubes were incubated with a 10 nM solution of the toxin for 30 min at room temperature without light. After this time the toxin was removed, they were washed, dried and placed on the slides with mounting medium.

Photographs were taken with a confocal microscope, using a 40× immersion objective and the number of AChR clusters was quantified using the image treatment software.

Table 2 provides details of the peptides which showed cluster inhibition values greater than 20%. Inhibition values were normalized with regards to the basal values of inhibition of the medium.

TABLE 2

Percentage of AChR cluster inhibition

| PEPTIDE | % INHIBITION |
| --- | --- |
| Control | 0.0% |
| Ac-L-Glu-L-Asp-L-Arg-L-Phe-L-Arg-L-Leu-NH$_2$ 10 μM | 20.8 |
| Ac-L-Asp-L-Asp-L-Tyr-L-Tyr-L-Lys-L-Met-NH$_2$ 10 μM | 21.5 |
| Ac-L-Glu-L-Asp-L-Arg-L-Phe-L-Lys-L-Leu-NH$_2$ 10 μM | 23.7 |
| Ac-L-Glu-L-Asp-L-Arg-L-Tyr-L-Arg-L-Leu-NH$_2$ 100 μM | 24.5 |
| H-L-Glu-L-Asp-L-Arg-L-Phe-L-Arg-L-Met-NH$_2$ 10 μM | 25.6 |
| Ac-L-Pro-L-Asp-L-Tyr-L-Phe-L-Lys-L-Leu-NH$_2$ 10 μM | 27.8 |
| Ac-L-Pro-L-Asp-L-Tyr-L-Phe-L-Arg-L-Leu-NH—(CH$_2$)$_{15}$—CH$_3$ 100 μM | 27.8 |
| Ac-L-Glu-L-Asp-L-Tyr-L-Phe-L-Arg-L-Leu-NH$_2$ 10 μM | 30.8 |
| Ac-L-Asp-L-Asp-L-Tyr-L-Tyr-L-Arg-L-Met-NH$_2$ 10 μM | 31.3 |
| Palm-L-Pro-L-Asp-L-Tyr-L-Tyr-L-Lys-L-Leu-NH$_2$ 10 μM | 33.7 |
| Ac-L-Asp-L-Asp-L-Tyr-L-Phe-L-Arg-L-Leu-NH$_2$ 10 μM | 33.8 |
| Ac-L-Glu-L-Asp-L-Tyr-L-Phe-L-Arg-L-Leu-OH 100 μM | 33.8 |
| Palm-L-Glu-L-Asp-L-Tyr-L-Tyr-L-Arg-L-Leu-NH$_2$ 10 μM | 34.8 |
| Ac-L-Pro-L-Asp-L-Tyr-L-Tyr-L-Lys-L-Leu-NH$_2$ 100 μM | 36.7 |
| Ac-L-Glu-L-Asp-L-Arg-L-Phe-L-Arg-L-Met-OH 100 μM | 39.1 |
| Ac-L-Pro-L-Asp-L-Arg-L-Tyr-L-Arg-L-Leu-NH$_2$ 100 μM | 40.2 |
| Ac-L-Pro-L-Asp-L-Tyr-L-Tyr-L-Lys-L-Met-NH$_2$ 10 μM | 40.7 |
| Ac-L-Pro-L-Asp-L-Arg-L-Tyr-L-Lys-L-Leu-NH$_2$ 100 μM | 43.6 |
| Ac-L-Pro-L-Asp-L-Arg-L-Phe-L-Lys-L-Leu-NH$_2$ 10 μM | 46.1 |
| Ac-L-Pro-L-Asp-L-Tyr-L-Tyr-L-Arg-L-Leu-NH$_2$ 10 μM | 51.9 |
| Ac-L-Glu-L-Asp-L-Arg-L-Phe-L-Arg-L-Met-NH$_2$ 100 μM | 55.1 |
| Ac-L-Glu-L-Asp-L-Tyr-L-Tyr-L-Arg-L-Leu-NH$_2$ 10 μM | 57.1 |
| Ac-L-Pro-L-Asp-L-Tyr-L-Tyr-L-Arg-L-Met-NH$_2$ 10 μM | 61.1 |
| Palm-L-Glu-L-Asp-L-Tyr-L-Tyr-L-Arg-L-Met-NH$_2$ 100 μM | 68.5 |

Example 9

Prophetic

Cosmetic Composition Containing Ac-L-Glu-L-Asp-L-Tyr-L-Tyr-L-Arg-L-Leu-NH$_2$

| INGREDIENT (INCI Nomenclature) | % IN WEIGHT |
| --- | --- |
| MINERAL OIL | 8.0 |
| STEARIC ACID | 2.4 |
| CETEARYL ALCOHOL | 1.6 |
| BEESWAX | 0.8 |
| GLYCERINE | 2.4 |
| CARBOMER | 0.3 |
| TRIETHANOLAMINE | 0.9 |
| Ac-L-Glu-L-Asp-L-Tyr-L-Tyr-L-Arg-L-Leu-NH$_2$ | 0.05 |
| PRESERVATIVES | 0.5 |

-continued

| INGREDIENT (INCI Nomenclature) | % IN WEIGHT |
|---|---|
| LECITHIN | 0.4 |
| AQUA (WATER) | q.s.p. 100 |

Example 10

Prophetic

Preparation of Liposomes Containing Ac-L-Pro-L-Asp-L-Tyr-L-Tyr-L-Lys-L-Leu-NH$_2$

| INGREDIENT (INCI Nomenclature) | % IN WEIGHT |
|---|---|
| PHOSPHATIDYLCHOLINE | 4.0 |
| Ac-L-Pro-L-Asp-L-Tyr-L-Tyr-L-Lys-L-Leu-NH$_2$ | 0.2 |
| PRESERVATIVES | 0.50 |
| AQUA (WATER) | q.s.p. 100 |

Dipalmitoylphosphatidylcholine (DPPC) is weighed and dissolved in chloroform. The solvent is evaporated under vacuum until a fine layer of phospholipid is obtained, and this layer is hydrated by treatment at 55° C. with an aqueous solution of the peptide at the desired concentration (containing the preservative Phenonip®), and the MLV liposomes are obtained. The ULV liposomes are obtained by submerging the MLV liposomes in an ultrasound bath at 55° C. for 8 cycles of 2 min at 5 min intervals. The size of the ULV liposomes is reduced by putting them through a high-pressure extrusion system.

Example 11

Prophetic

Composition of a Facial Cream Containing Ac-L-Pro-L-Asp-L-Arg-L-Phe-L-Lys-L-Leu-NH$_2$

| INGREDIENT (INCI Nomenclature) | % IN WEIGHT |
|---|---|
| *BUTYROSPERMUM PARKII* | 3.5-4.5 |
| CETEARYL ETHYLHEXANOATE | 3-5 |
| GLYCERYL STEARATE S.E. | 1.5-2.5 |
| SQUALANE | 0.5-1 |
| PEG-100 STEARATE | 1 |
| POLYSORBATE 60 | 0.30 |
| CETYL PALMITATE | 1.5-2.5 |
| DIMETHICONE | 2.5-3.5 |
| CETEARYL ALCOHOL | 1.5-2.5 |
| PALMITIC ACID | 0.5 |
| GLYCERIN | 1.5-2.5 |
| BUTYLENE GLYCOL | 1-3 |
| MANNITOL | 0.5-1.5 |
| HYDROGENATED LECITHIN | 0.5-1.5 |
| PROPYLENE GLYCOL | 0.5-1.5 |
| CARBOMER | 0.4 |
| ETHYLHEXYL PALMITATE | 1.5-2.5 |
| TROMETHAMINE | 0.4 |
| PRESERVATIVES | q.s. |
| Ac-L-Pro-L-Asp-L-Arg-L-Phe-L-Lys-L-Leu-NH$_2$ | 0.001 |
| AQUA (WATER) | q.s.p. 100 |

Example 12

Prophetic

Preparation of a Composition in the Form of a Liposome Gel Containing Ac-L-Pro-L-Asp-L-Tyr-L-Tyr-L-Lys-L-Leu-NH$_2$ The liposomes of Example 11 are dispersed in water with the preservatives (EDTA, imidazolidinyl urea and Phenonip®) under light stirring. Hispagel® 200 is added [INCI: Aqua (Water), glycerin, glyceryl polyacrylate] and is slightly stirred until a homogenous mixture is obtained.

| INGREDIENT (INCI Nomenclature) | % IN WEIGHT |
|---|---|
| LIPOSOMES CONTAINING 1% Ac-L-Pro-L-Asp-L-Tyr-L-Tyr-L-Lys-L-Leu-NH$_2$ | 10.00 |
| DISODIUM EDTA | 0.15 |
| IMIDAZOLIDINYL UREA | 0.10 |
| PRESERVATIVE | 0.50 |
| AQUA (WATER) | 29.25 |
| AQUA (WATER), GLYCERIN, GLYCERYL POLYACRYLATE | 60.00 |

Example 13

Prophetic

Composition of a Microemulsion Containing Palm-L-Glu-L-Asp-L-Tyr-L-Tyr-L-Arg-L-Met-NH$_2$

| INGREDIENT (INCI Nomenclature) | % IN WEIGHT |
|---|---|
| DIETHYLHEXYL SODIUM SULFOSUCCINATE | 1.35 |
| ISOSTEARIC ACID | 7.65 |
| AQUA (WATER) | 0.2 |
| ALCOHOL DENAT | 0.8 |
| Palm-L-Glu-L-Asp-L-Tyr-L-Tyr-L-Arg-L-Met-NH$_2$ | 0.005 |
| ETHYLHEXYL COCOATE | q.s.p. 100 |

Example 14

Prophetic

Preparation of a Composition of Mixed Micelles Containing Ac-L-Glu-L-Asp-L-Tyr-L-Tyr-L-Arg-L-Leu-NH$_2$ The ingredients of phase A are weighed and warmed slightly to about 30° C. to help to dissolve some of the preservatives in a vessel suitable for the complete sample. Next, phase B components are added and homogenized under light stirring.

Phase C is then added under continuous stirring, after which phase D is added with slow stirring to avoid foaming. The pH is adjusted to 5.5-6.5.

| | INGREDIENT (INCI Nomenclature) | % IN WEIGHT |
|---|---|---|
| A | AQUA (WATER) | q.s.p. 100 |
| A | PHENOXYETHANOL | 0.5 |
| A | CAPRILYL GLYCOL | 0.5 |
| A | POTASSIUM SORBATE | 0.3 |

-continued

| | INGREDIENT (INCI Nomenclature) | % IN WEIGHT |
|---|---|---|
| B | AQUA (WATER) | 27.5 |
| B | Ac-L-Glu-L-Asp-L-Tyr-L-Tyr-L-Arg-L-Leu-NH$_2$ | 0.025 |
| B | LECITHIN | 4.0 |
| C | XANTHAN GUM | 0.4 |
| D | AQUA (WATER), CAPRILYL/CAPRYL GLUCOSIDE | 30 |

Example 15

Composition of a Cream Containing Ac-L-Glu-L-Asp-L-Tyr-L-Tyr-L-Arg-L-Leu-NH$_2$

| INGREDIENT (INCI Nomenclature) | % IN WEIGHT |
|---|---|
| WATER (AQUA) | q.s.p. 100 |
| CAPRYLIC/CAPRIC TRIGLYCERIDE | 8 |
| GLYCERYL STEARATE, PEG-100 STEARATE | 6 |
| ISOHEXADECANE | 3 |
| PROPYLENE GLYCOL | 2 |
| STEARIC ACID, PALMITIC ACID | 1.8 |
| Ac-L-Glu-L-Asp-L-Tyr-L-Tyr-L-Arg-L-Leu-NH$_2$ | 0.0025 |
| LECITHIN | 0.1 |
| ARGININE | 0.001 |
| CETYL ALCOHOL | 0.7 |
| ACRYLATES/C10-30 ALKYL ACRYLATE CROSSPOLYMER | 0.15 |
| TRIETHANOLAMINE | q.s. |
| DISODIUM EDTA | 0.0075 |
| IMIDAZOLIDINYL UREA | 0.3 |
| PRESERVATIVES | 0.85 |

Example 16

Effect of the Composition from Example 15 in the Reduction of Wrinkles

To assess the effectiveness of the composition from Example 15 of the invention, a panel of 20 volunteers with an average age of 45 years applied the composition from Example 15 twice a day to the periorbital area of one eye for a month, whilst a placebo cream, with the same composition as the cream in Example 15 but without the peptide of the invention, was applied to the periorbital area of the other eye. The depth of the wrinkles was assessed before and after the treatment using the Primos optical 3D technique, and the wrinkle reduction effectiveness was calculated in relation to the effectiveness shown by the placebo cream. A 44.7% increase in the average reduction of the depth of the wrinkles on the volunteers was obtained with regards to the placebo cream values.

The invention claimed is:

1. A peptide of general formula (I)

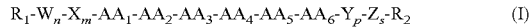

its stereoisomers, mixtures thereof and/or its cosmetic or pharmaceutically acceptable salts, wherein:
$AA_1$ is selected from the group consisting of -Asp-, -Glu- and -Pro-;
$AA_2$ is -Asp-;
$AA_3$ is selected from the group consisting of -Tyr- and -Arg-;
$AA_4$ is selected from the group consisting of -Phe- and -Tyr-;
$AA_5$ is selected from the group consisting of -Arg- and -Lys-;
$AA_6$ is selected from the group consisting of -Leu- and -Met-;
W, X, Y and Z are independently selected from amongst themselves from the group consisting of coded amino acids and non-coded amino acids;
n, m, p and s are independently selected from amongst themselves and have a value of between 0 and 1;
$R_1$ is selected from the group consisting of H, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group consisting of H, substituted or unsubstituted non-cyclic aliphatic groups, substituted or unsubstituted alicyclyl, substituted or unsubstituted aryl, substituted or unsubstituted aralkyl, substituted or unsubstituted heterocyclyl, and substituted or unsubstituted heteroarylalkyl; and
$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, and substituted or unsubstituted aralkyl.

2. The peptide according to claim 1, wherein $R_1$ is selected from the group consisting of H and $R_5$—CO—, wherein $R_5$ is selected from the group consisting of substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members, and substituted or unsubstituted heteroarylalkyl having 2 to 24 carbon atoms and 1 to 3 atoms other than carbon and an alkyl chain of 1 to 6 carbon atoms.

3. The peptide according to claim 2, wherein $R_1$ is selected from the group consisting of H, acetyl, tert-butanoyl, hexanoyl, 2-methylhexanoyl, cyclohexancarboxyl, octanoyl, decanoyl, lauroyl, myristoyl, palmitoyl, stearoyl, oleoyl and linoleoyl.

4. The peptide according to claim 1, wherein $R_2$ is —$NR_3R_4$ or —$OR_3$, wherein $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members, and substituted or unsubstituted heteroarylalkyl having 2 to 24 carbon atoms and 1 to 3 atoms other than carbon and an alkyl chain of 1 to 6 carbon atoms.

5. The peptide according to claim 4, wherein $R_3$ and $R_4$ are independently selected from the group consisting of H, methyl, ethyl, hexyl, dodecyl and hexadecyl.

6. The peptide according to claim 1, wherein $R_1$ is selected from the group consisting of H, acetyl, lauroyl, myristoyl and palmitoyl, $AA_1$ is -L-Glu-, $AA_2$ is -L-Asp-, $AA_3$ is -L-Tyr-, $AA_4$ is -L-Tyr-, $AA_5$ is -L-Arg-, $AA_6$ is -L-Leu-, and $R_2$ is —$NR_3R_4$ or —$OR_3$, wherein $R_3$ and $R_4$ are independently selected from H, methyl, ethyl, hexyl, dodecyl and hexadecyl.

7. The peptide according to claim 1, wherein $R_1$ is selected from the group consisting of H, acetyl, lauroyl, myristoyl and palmitoyl, $AA_1$ is -L-Pro-, $AA_2$ is -L-Asp-, $AA_3$ is -L-Tyr-, $AA_4$ is -L-Tyr-, $AA_5$ is -L-Lys-, $AA_6$ is -L-Leu-, and $R_2$ is —$NR_3R_4$ or —$OR_3$, wherein $R_3$ and $R_4$ are independently selected from H, methyl, ethyl, hexyl, dodecyl and hexadecyl.

8. The peptide according to claim 1, wherein $R_1$ is selected from the group consisting of H, acetyl, lauroyl, myristoyl and palmitoyl, $AA_1$ is -L-Glu-, $AA_2$ is -L-Asp-, $AA_3$ is -L-Arg-, $AA_4$ is -L-Phe-, $AA_5$ is -L-Arg-, $AA_6$ is -L-Met- and $R_2$ is —$NR_3R_4$ or —$OR_3$, wherein $R_3$ and $R_4$ are independently selected from H, methyl, ethyl, hexyl, dodecyl and hexadecyl.

9. The peptide according to claim 1, wherein $R_1$ is selected from the group consisting of H, acetyl, lauroyl, myristoyl and palmitoyl, $AA_1$ is -L-Glu-, $AA_2$ is -L-Asp-, $AA_3$ is -L-Tyr-, $AA_4$ is -L-Tyr-, $AA_5$ is -L-Arg-, $AA_6$ is -L-Met-, and $R_2$ is $NR_3R4$ or $OR_3$ wherein $R_3$ and $R_4$ are independently selected from H, methyl, ethyl, hexyl, dodecyl and hexadecyl.

10. The peptide according to claim 1, where $R_1$ is selected from the group consisting of H, acetyl, lauroyl, myristoyl and palmitoyl, $AA_1$ is -L-Pro-, $AA_2$ is -L-Asp-, $AA_3$ is -L-Tyr-, $AA_4$ is -L-Tyr-, $AA_5$ is -L-Arg-, $AA_6$ is -L-Met-, and $R_2$ is —$NR_3R_4$ or —$OR_3$, wherein $R_3$ and $R_4$ are independently selected from H, methyl, ethyl, hexyl, dodecyl and hexadecyl.

11. The peptide according to claim 1, wherein $R_1$ is selected from the group consisting of H, acetyl and palmitoyl and $R_2$ is selected from the group consisting of —OH and —$NH_2$.

12. A process for the preparation of a peptide of general formula (I), its stereoisomers, mixtures thereof and/or its cosmetically or pharmaceutically acceptable salts, according to claim 1, wherein the process is carried out in solid phase or in solution.

13. A cosmetic or pharmaceutical composition which comprises a cosmetically or pharmaceutically effective amount of at least one peptide of general formula (I), its stereoisomers, mixtures thereof and/or its cosmetically or pharmaceutically acceptable salts, according to claim 1, and at least one cosmetically or pharmaceutically acceptable excipient or adjuvant.

14. The composition according to claim 13, wherein the peptide of general formula (I), its stereoisomers, mixtures thereof and/or its cosmetically or pharmaceutically acceptable salts, is at a concentration between 0.000001% and 20% by weight, with regards to the total weight of the composition.

15. The composition according to claim 13, wherein said peptide of general formula (I), its stereoisomers, mixtures thereof and/or its cosmetically or pharmaceutically acceptable salts, is incorporated into a cosmetic or pharmaceutical delivery system and/or sustained release system selected from the group consisting of liposomes, mixed liposomes, oleosomes, niosomes, ethosomes, millicapsules, microcapsules, nanocapsules, sponges, cyclodextrins, vesicles, micelles, mixed micelles of surfactants, mixed micelles of surfactant-phospholipid, millispheres, microspheres, nanospheres, liposheres, microemulsions, nanoemulsions, miniparticles, milliparticles, microparticles, nanoparticles, solid lipid nanoparticles and nanostructured lipid carriers or is adsorbed on a cosmetically or pharmaceutically acceptable solid organic polymer or solid mineral support selected from the group consisting of talc, bentonite, silica, starch and maltodextrin.

16. The composition according to claim 13, wherein it is presented in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, soft capsules, hard capsules, tablets, sugar coated tablets, granules, chewing gum, solutions, suspensions, emulsions, syrups, polysaccharide films, jellies and gelatins.

17. The composition according to claim 13, wherein said composition is incorporated into a product selected from the group consisting of under-eye concealers, make-up foundation, make-up removing lotions, make-up removing milks, eye shadows, lipsticks, lip gloss, lip protectors and powders.

18. The composition according to claim 13, wherein the peptide of general formula (I), its stereoisomers, mixtures thereof and/or its cosmetically or pharmaceutically acceptable salts, is incorporated into a fabric, a non-woven fabric or a medical device.

19. The composition according to claim 13, wherein the composition further comprises a cosmetically or pharmaceutically effective amount of at least one adjuvant selected from the group of other agents inhibiting acetylcholine receptor clustering, other agents inhibiting muscle contraction, anticholinergic agents, elastase inhibiting agents, matrix metalloproteinase inhibiting agents, melanin synthesis stimulating and inhibiting agents, whitening or depigmenting agents, propigmenting agents, self-tanning agents, anti-aging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl specie scavengers, anti-glycation agents, antihistamine agents, antiemetic agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, epidermal hydrolytic enzymes, vitamins, pigments or colorants, dyes, gelling polymers, thickeners, surfactants, softening agents, anti-wrinkle agents, agents able to reduce or treat bags under the eyes, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, aquaporin synthesis-stimulation agents, hyaluronic acid synthesis-stimulating agents, fibronectin synthesis-stimulating agents, sirtuin synthesis-stimulating agents, agents stimulating the synthesis of lipids and components of the stratum corneum, agents stimulating the synthesis of ceramides, agents that inhibit collagen degradation, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, antihyperkeratosis agents, comedolytic agents, antipsoriasis agents, DNA repair agents, DNA protecting agents, stabilizers, anti-itching agents, agents for the treatment and/or care of sensitive skin, firming agents, anti-stretch mark agents, astringent agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents and/or analgesics, anaesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, preservatives, perfumes, chelating agents, vegetable extracts, essential oils, marine extracts, agents obtained from a biofermentation process, mineral salts, cell extracts and sunscreens, active organic or mineral photoprotective agents against ultraviolet A and/or B rays, and combinations thereof.

20. A method of treatment and/or care of the skin, which comprises administering to the skin an effective amount of at least one peptide according to claim 1.

21. The method according to claim 20, in which said treatment and/or care of the skin is the treatment of the signs of aging and/or photoaging.

22. The method according to claim 20, in which said treatment and/or care of the skin is a treatment of skin affected by wrinkles and/or expression lines.

* * * * *